US011319530B2

(12) United States Patent
Beckwith et al.

(10) Patent No.: US 11,319,530 B2
(45) Date of Patent: May 3, 2022

(54) HOST CELLS AND SYSTEMS FOR MEMBRANE PROTEIN EXPRESSION

(71) Applicant: President and Fellows of Harvard College, Cambridge, MA (US)

(72) Inventors: Jonathan Beckwith, Cambridge, MA (US); Dana Boyd, Medford, MA (US); Jessica Blazyk, Somerville, MA (US); Feras Hatahet, Burlingame, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 244 days.

(21) Appl. No.: 15/977,788

(22) Filed: May 11, 2018

(65) Prior Publication Data

US 2018/0312816 A1 Nov. 1, 2018

Related U.S. Application Data

(63) Continuation of application No. PCT/US2016/061509, filed on Nov. 11, 2016.

(60) Provisional application No. 62/255,162, filed on Nov. 13, 2015.

(51) Int. Cl.
*C12N 9/52* (2006.01)
*C07K 14/195* (2006.01)
*C12N 9/04* (2006.01)
*C07K 14/705* (2006.01)
*C12P 21/02* (2006.01)
*C12N 9/02* (2006.01)
*C12N 9/90* (2006.01)
*G01N 33/50* (2006.01)
*C07K 14/245* (2006.01)
*C12N 1/20* (2006.01)
*C12R 1/19* (2006.01)

(52) U.S. Cl.
CPC .......... *C12N 9/0006* (2013.01); *C07K 14/245* (2013.01); *C07K 14/705* (2013.01); *C12N 9/0051* (2013.01); *C12N 9/52* (2013.01); *C12N 9/90* (2013.01); *C12P 21/02* (2013.01); *C12Y 101/04001* (2013.01); *G01N 33/5041* (2013.01); *C12N 1/205* (2021.05); *C12R 2001/19* (2021.05); *G01N 2333/904* (2013.01)

(58) Field of Classification Search
None
See application file for complete search history.

(56) References Cited

U.S. PATENT DOCUMENTS

2011/0097737 A1* 4/2011 Samuelson ............ C07K 14/47
435/7.4

FOREIGN PATENT DOCUMENTS

WO WO-2010/045381 A2 4/2010
WO WO-2012/088222 A2 6/2012
WO WO-2012/104494 A1 8/2012

OTHER PUBLICATIONS

Ziemann et al. Gene name errors are widespread in the scientific literature. 2016. Genome Biology. vol. 17, No. 177, 3 pages. (Year: 2016).*
Mandela, Eric. The role of YidC in the assembly of Rat VKORC1 in the inner membrane of *Escherichia coli*. Published Oct. 13, 2015. University of OULU, Faculty of Biochemistry and Molecular Medicine, Biochemistry. 99 pages. (Year: 2015).*
Wickles et al. A structural model of the active ribosome-bound membrane protein insertase YidC. Jul. 10, 2014. eLife. 3:e03035. pp. 1-17. (Year: 2014).*
Boyd et al., "The role of charged amino acids in the localization of secreted and membrane proteins," Cell, 62(6): 1031-1033 (1990).
Hatahet et al., "Altered *Escherichia coli* membrane protein assembly machinery allows proper membrane assembly of eukaryotic protein vitamin K epoxide reductase," Proc Natl Acad Sci U S A, 112(49): 15184-15189 (2015).
International Search Report and Written Opinion for International Application No. PCT/US2016/061509 dated Apr. 11, 2017.
Jaenecke et al., "Membrane composition influences the activity of in vitro refolded human vitamin K epoxide reductase," Biochemistry, 54(42): 6454-6461 (2015).
Jaenecke et al., "Supporting information: Membrane composition influences the activity of in vitro refolded human vitamin K epoxide reductase," Biochemistry, p. 6454, XP055357513 (2015).
Nannenga et al., "Reprogramming chaperone pathways to improve membrane protein expression in *Escherichia coli*," Protein Sci, 20(8): 1411-1420 (2011).
Raine et al., "Targeting and insertion of heterologous membrane proteins in *E. coli*," Biochimie, 85(7): 659-668 (2003).
Tie et al., "Human vitamin K epoxide reductase and its bacterial homologue have different membrane topologies and reaction mechanisms", J Biol Chem, 287(41): 33945-33955 (2012).
Wang et al., "Supplementary data to: Membrane topology and mutational analysis of mycobacterium tuberculosis VKOR, a protein involved in disulfide bond formation and a homologue of human vitamin K epoxide reductase," Antioxid Redox Signal, 14(8): 1413-1420 (2011).
Wang et al., "Membrane topology and mutational analysis of *Mycobacterium tuberculosis* VKOR, a protein involved in disulfide bond formation and a homologue of human vitamin K epoxide reductase," Antioxid Redox Signal, 14(8): 1413-1420 (2011).

* cited by examiner

*Primary Examiner* — Channing S Mahatan
(74) *Attorney, Agent, or Firm* — Foley Hoag LLP; DeAnn F. Smith; Allison L. Gilder

(57) ABSTRACT

Provided herein are host cells or host cellular expression systems that express a membrane protein. Also, methods are provided that use such host cells or host cellular expression systems to produce higher amounts of the membrane proteins. Further, the cells or cellular systems can be used as tools for the functional characterization of membrane proteins, as well as for screening and drug discovery efforts targeting membrane proteins.

11 Claims, 16 Drawing Sheets

Specification includes a Sequence Listing.

A

B

C

D

A

B

A

B

SEQ ID NO: 2

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Thr Gly Gly Gly Ser Gly Gly Gly Ser Gly Ser
1               5                   10

<210> SEQ ID NO 2
<211> LENGTH: 161
<212> TYPE: PRT
<213> ORGANISM: Rattus norvegicus

<400> SEQUENCE: 2

Met Gly Thr Thr Trp Arg Ser Pro Gly Arg Leu Arg Leu Ala Leu Cys
1               5                   10                  15

Leu Ala Gly Leu Ala Leu Ser Leu Tyr Ala Leu His Val Lys Ala Ala
                20                  25                  30

Arg Ala Arg Asn Glu Asp Tyr Arg Ala Leu Cys Asp Val Gly Thr Ala
            35                  40                  45

Ile Ser Cys Ser Arg Val Phe Ser Ser Arg Trp Gly Arg Gly Phe Gly
        50                  55                  60

Leu Val Glu His Val Leu Gly Ala Asp Ser Ile Leu Asn Gln Ser Asn
65                  70                  75                  80

Ser Ile Phe Gly Cys Met Phe Tyr Thr Ile Gln Leu Leu Leu Gly Cys
                85                  90                  95

Leu Arg Gly Arg Trp Ala Ser Ile Leu Leu Ile Leu Ser Ser Leu Val
            100                 105                 110

Ser Val Ala Gly Ser Leu Tyr Leu Ala Trp Ile Leu Phe Phe Val Leu
        115                 120                 125

Tyr Asp Phe Cys Ile Val Cys Ile Thr Thr Tyr Ala Ile Asn Ala Gly
    130                 135                 140

Leu Met Leu Leu Ser Phe Gln Lys Val Pro Glu His Lys Val Lys Lys
145                 150                 155                 160

Pro
```

HOST CELLS AND SYSTEMS FOR MEMBRANE PROTEIN EXPRESSION

CROSS-REFERENCE TO RELATED APPLICATION

This application is a Continuation Application of PCT/US2016/061509, filed on Nov. 11, 2016, which claims the benefit of U.S. Provisional Application No. 62/255,162, filed on Nov. 13, 2015; the entire contents of said applications are incorporated herein in their entirety by this reference.

SEQUENCE LISTING

The instant application contains a Sequence Listing which has been submitted electronically in ASCII format and is hereby incorporated by reference in its entirety. Said ASCII copy, created on Feb. 15, 2017, is named HMV-254_25_SL.txt and is 2,029 bytes in size.

TECHNICAL FIELD

The disclosure relates to the field of protein expression technologies. More specifically, host cells or host cellular expression systems are provided that express a foreign membrane protein in the host cell. Also, methods are provided that use such host cells or host cellular expression systems to produce higher amounts of the membrane proteins. Further, the cells or cellular systems can be used as tools for the structural and functional characterization of membrane proteins, as well as for screening and drug discovery efforts targeting membrane proteins.

BACKGROUND

While proteins localized to biological membranes constitute about a quarter of the products of an organism's open reading frames, only 0.1% of known protein structures are membrane proteins (1, 2). The lag in our knowledge of the physiology and structural biology of membrane proteins is due to many factors including the low expression levels of membrane proteins and the complex biophysical nature of their interactions at the water/lipid interface. Membrane proteins, which have one or more segments that traverse the lipid bilayer, require dedicated cellular machineries for their targeting to and integration into the membranes (3). Even though these cellular machineries have maintained conserved features in all domains of life, efforts to express membrane proteins in foreign organisms have often been unsuccessful. In many cases, the overexpression of indigenous membrane proteins leads to mis-targeting and inclusion body formation, protein degradation or cell death (4).

Promoting the correct orientation of proteins within the membrane provides an additional challenge to the insertion machinery. Proper assembly is a crucial step in the folding pathway of a membrane protein since a wrong orientation could be detrimental to functioning of the protein and to the viability of the cell. The overall architecture of a membrane protein, including its final membrane topology, is achieved by topogenic signals embedded in the amino acid sequence. Such signals include long stretches of mostly hydrophobic amino acids (around 20) that determine the portion of the protein to be embedded in the membrane. Furthermore, the abundance of positively-charged amino acids in cytoplasmic domains of membrane proteins, generally referred to as the positive-inside rule, is a major contributor to membrane protein topology (5,6).

Most membrane proteins express at low levels in non-engineered eukaryotic or bacterial cells. Different techniques to increase the expression levels of the membrane protein have been taken to enhance membrane protein surface expression in heterologous cells, including addition/deletion of receptor sequences, co-expression with interacting proteins, and treatment with pharmacological chaperones (reviewed in Dunham and Hall, 2009, Trends Biotechnol. 27:541). It remains a challenge, however, to significantly improve total yield, conformational stability and/or functionality of expressed membrane protein.

Thus, it would be advantageous to have alternative expression systems that permit heterologous expression of membrane proteins for isolation, purification, and structural studies. Likewise, it would be advantageous to have membrane proteins in a functional form for screening assays targeting membrane proteins. This would greatly facilitate the whole trajectory of drug discovery efforts on membrane proteins as therapeutic targets.

SUMMARY

Proteins embedded in biological membranes are important targets for therapeutic intervention. However, they tend to be far more challenging to deal with than soluble proteins. Provided herein is a host cell (e.g., *E. coli*) useful for the high-level expression of exogenous (e.g., foreign) membrane proteins (e.g., vitamin K epoxide reductase (VKORc1) in functional form.

Thus, one aspect of the invention relates to a host cell comprising: an exogenous nucleic acid molecule encoding a membrane protein (e.g., vitamin K epoxide reductase (VKORc1), said membrane protein comprises at least one mutation (e.g., VKORc1$_{AAAR}$); and at least one host cell-specific mutation in gene selected from a disulfide bond enzyme (e.g., dsbB or dsbA), insertase (e.g., yidC), ubiquinone biosynthesis gene (e.g., ubiC or ubiE), menaquinone biosynthesis gene (e.g., menA), or cytoplasmic protease (e.g., hsIV or hsIU), or combinations thereof.

In some embodiments, the host cell is a bacterial host cell.

In some embodiments, the host cell is a *Escherichia coli*.

In some embodiments, the nucleic acid molecule is derived from a mouse, rat, rabbit, hamster, gerbil, dog, cat, goat, pig, cow, horse, whale, monkey, or human.

In some embodiments, the membrane protein has at least two, three, four, five, or six mutations.

In some embodiments, the host cell has at least two, three, four, five, or six host cell-specific mutations.

In some embodiments, the mutation is a deletion, substitution, or insertion.

In some embodiments, the membrane protein is selected from the group consisting of vitamin K epoxide reductase (VKORc1), proteorhodopsin, G protein couple receptors, growth factor receptors, transmembrane ion channels, neurotransmitter transporters, serotonin and olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, histamine receptors, protease-activated receptors, rhodopsins, CXCR4, GPR3, rhodopsin, vasopressin receptor, β1 adrenergic receptor, β2 adrenergic receptor, β3 adrenergic receptor, α1 adrenergic receptors and the α2 adrenergic receptor, M1 muscarinic receptor, M2 muscarinic receptor, M3 muscarinic receptor, M4 muscarinic receptor, M5 muscarinic receptor, and angiotensin II receptors.

In some embodiments, the membrane protein is VKORc1.

In some embodiments, the VKORc1 comprises a mutation having a deletion of amino acid 31-33 (AAR) (VKORc1$_{\Delta AAR}$).

In some embodiments, the VKORc1 comprises a mutation at a residue selected from the group consisting of glycine 60 to aspartic acid (G60D), cysteine 43 to alanine (C43A), cysteine 51 to alanine (C51A), cysteine 132 to alanine (C33A), valine 29 to glutamic acid (V29E), valine 29 to lysine (V29K), arginine 33 to proline (A33P), alanine 48 to serine (A48S), arginine 53 to histidine (R53H), phenylalanine 55 to serine (F55S), serine 57 to proline (S57P), serine 57 to phenylalanine (S57F), arginine 58 to histidine (R58H), serine 52 to asparagine (S52N), arginine 61 to histidine (R61H), glycine 62 to aspartic acid (G62D), glycine 64 to aspartic acid (G64D), threonine 4 to isoleucine (T4I), leucine 65 to proline (L65P), asparagine 80 to aspartic acid (N80D), threonine 137 to proline (T137P), or combination thereof.

In some embodiments, the VKORc1 comprises two mutations G60D and VKORc1$_{\Delta AAR}$.

In some embodiments, the at least one host cell-specific mutation is a mutation of at least one gene selected from the group consisting of a disulfide bond enzyme, insertase, ubiquinone biosynthesis gene, menaquinone biosynthesis gene, and cytoplasmic protease.

In some embodiments, the disulfide bond enzyme is dsbB or dsbA.

In some embodiments, the insertase is yidC.

In some embodiments, the cytoplasmic protease is hsIV or hsIU.

In some embodiments, the ubiquinone biosynthesis gene is selected from ubiC or ubiE.

In some embodiments, the menaquinone biosynthesis gene is menA.

In some embodiments, the yidC comprises a mutation at a residue selected from the group consisting of alanine 11 to threonine (A11T), threonine 362 to isoleucine (T362I), threonine 362 to alanine (T362A), threonine 362 to serine (T362S), threonine 362 to phenylalanine (T362F), threonine 362 to valine (T362V), threonine 362 to leucine (T362L), threonine 362 to glutamic acid (T362E), threonine 362 to arginine (T362R), threonine 362 to asparagine (T362N), threonine 362 to aspartic acid (T362D), threonine 362 to cysteine (T362C), threonine 362 to glutamine (T362Q), threonine 362 to glycine (T362G), threonine 362 to histidine (T362H), threonine 362 to methionine (T362M), threonine 362 to proline (T362P), threonine 362 to tryptophan (T362W), threonine 362 to tyrosine (T362Y), threonine 362 to lysine (T362K), arginine 366 to isoleucine (R366I), threonine 373 to isoleucine (T373I), glutamine 429 to isoleucine (Q429I), threonine 474 to isoleucine (T474I), glycine 512 to serine (G512S), serine 520 to isoleucine (S520I), asparagine 521 to isoleucine (N521I), and glutamine 527 to isoleucine (Q527I), or combination thereof.

In some embodiments, the yidC comprises a mutation at T362I.

In some embodiments, the yidC comprises a double mutation at T362I and T373I.

In some embodiments, the yidC comprises a double mutation at T362I and G512S.

In some embodiments, the yidC comprises a mutation at T362D, T362C, T362Q, T362G, T362H, T362M, T362P, T362W, T362Y, T362N, or T362R supplemented with a plasmid coding for YidC$_{WT}$.

In some embodiments, the hsIV comprises a mutation at residue cysteine 160 to tyrosine (C160Y) or threonine 163 to isoleucine (T163I).

In some embodiments, the mutation is a deletion of hsIV or hsIU.

In some embodiments, the mutation is a deletion of dsbB or dsbA.

In some embodiments, the dsbA comprises a mutation at residue cysteine 33 to alanine (C33A).

In some embodiments, the mutation is a deletion of menA.

In some embodiments, the host cell further comprises a reporter.

In some embodiments, the reporter is β-galactosidase.

In some embodiments, the β-galactocidase is a disulfide-bond sensitive enzyme.

In some embodiments, the disulfide-bond sensitive enzyme is β-gal$^{dbs}$.

In some embodiments, the exogenous nucleic acid molecule is under the control of a promoter.

In some embodiments, the promoter is a constitutive promoter or an inducible promoter.

In some embodiments, the inducible promoter is an isopropyl β-D thiogalactopyranoside (IPTG)-inducible promoter.

A cell culture of the host cell is also provided. Another aspect of the invention relates to a polypeptide expressed by said host cell or a membrane preparation of said host cell. Another aspect of the invention relates a method of inhibitor, ligand screening, drug screening, protein capturing, protein purification, immunization, or a biophysical study, wherein the improvement comprises: utilizing said host cell, for inhibitor, ligand screening, drug screening, protein capturing and purification, immunization, biophysical studies.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description

BRIEF DESCRIPTION OF FIGURES

FIG. 12 shows chromosomal directed mutagenesis in the hydrophilic groove of YidC. Overnight cultures of yidC mutants (derived from HK325) carrying a VKORc1$_{AAAR}$ plasmid were serially diluted then spotted on M63 minimal plates containing X-Gal or TCEP (0, 8 and 10 mM).

DETAILED DESCRIPTION

Definitions

Figure 1:
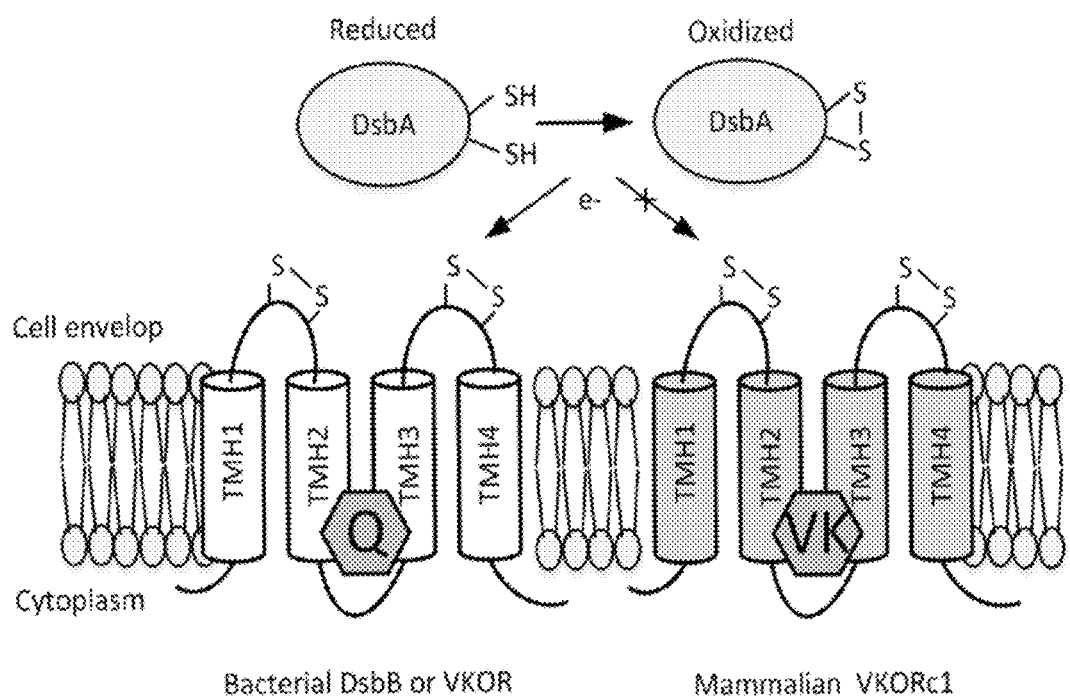
FIG. 1 shows disulfide bond formation in *E. coli* is promoted by EcDsbB and MtbVKOR but not by vertebrate VKORc1. DsbB and VKOR are inner membrane proteins promote disulfide bond formation in the bacterial cell envelop. They share similar overall reaction mechanisms and complement each other in oxidizing DsbA. Q stands for quinone and VK for vitamin K (also a quinone). However, VKORc1, the mammalian homologue of the bacterial VKOR, is dysfunctional when expressed in *E. coli*.

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a membrane protein, a deletion can involve deletion of about 2, about 5, about 10, up to about 20, up to about 30 or up to about 50 or more amino acids. A protein or a fragment thereof may contain more than one deletion.

The term "endogenous," as used herein, refers to substances (e.g., genes) originating from within an organism, tissue, or cell. Analogously, "exogenous," as used herein, is any material that is foreign to or comes from outside an organism, tissue, or cell, but that is present (and typically can become active) in that organism, tissue, or cell.

The term "host cell" and equivalent terms like "recombinant host cell," "expression host cell," "expression host system," "expression system," as used herein, is intended to refer to a cell into which a foreign or exogenous nucleic acid molecule encoding a membrane protein has been introduced, and in which chromosomal mutations or host-cell specific mutations have been engineered. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell," as used herein. A recombinant host cell may be an isolated cell or cell line grown in culture. Particular examples are provided further herein.

An "insertion" or "addition" is that change in an amino acid or nucleotide sequences, which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a membrane protein or a fragment thereof, an insertion or addition is usually of about 1, about 3, about 5, about 10, up to about 20, up to about 30 or up to about 50 or more amino acids. A protein or fragment thereof may contain more than one insertion.

The "membrane protein," as used herein, refers to a protein that is attached to or associated with a membrane of a cell or an organelle. In some embodiments, the membrane protein is a polytopic membrane protein, vitamin K epoxide reductase, that that perform electron transfer processes, i.e., receive electrons from thioredoxin-like proteins and transfer those electrons to membrane-localized quinones. Specific non-limiting examples are provided further in the specification.

As use herein, a "mutation" refers to a change to any substitution, deletion, addition, insertion, or genetic modification of the membrane protein, host cell, or host cell chromosomes. Said mutations may be introduced via DNA and protein recombination techniques known in the art. Said mutations may also be introduced via expression of a exogenous plasmid containing said mutations, or via bacterial transduction techniques known in the art, e.g., P1 transduction.

A "substitution," as used herein, results from the replacement of one or more amino acids or nucleotides by different amino acids or nucleotides, respectively, as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

The term "compound" or "test compound" or "candidate compound" or "drug candidate compound," as used herein, describes any molecule, either naturally occurring or synthetic that is tested in an assay, such as a screening assay or drug discovery assay. As such, these compounds comprise organic or inorganic compounds. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies, antibody fragments or antibody conjugates. In some embodiments, the test compounds can be inhibitors, such as anticoagulants. Test compounds can also be protein scaffolds. For high-throughput purposes, test compound libraries may be used, such as combinatorial or randomized libraries that provide a sufficient range of diversity. Examples include, but are not limited to, natural compound libraries, allosteric compound libraries, peptide libraries, antibody fragment libraries, synthetic compound libraries, fragment-based libraries, phage-display libraries, and the like. A more detailed description can be found further in the specification.

As used herein, the term "ligand" means a molecule that specifically binds to a membrane protein, either intracellularly or extracellularly. A ligand may be, without the purpose of being limitative, a protein, a (poly)peptide, a lipid, a small molecule, a protein scaffold, a nucleic acid, an ion, a carbohydrate, an antibody or an antibody fragment, such as a nanobody (all as defined herein). A ligand may be synthetic or naturally occurring. A ligand also includes a "native ligand," which is a ligand that is an endogenous, natural ligand for a native protein. Usually, a membrane protein will adopt a particular conformation upon binding of a ligand. Thus, a ligand is also referred to herein as a "conformation-selective ligand" or "conformation-specific ligand." The term includes agonists, full agonists, partial agonists, inverse agonists, and antagonists, binding at either the orthosteric site or at an allosteric site.

As used herein, an "agonist" refers to a ligand that, by binding a membrane protein, increases the membrane protein's activity. Full agonists are capable of maximal protein stimulation; partial agonists are unable to elicit full activity even at saturating concentrations. Partial agonists can also function as "blockers" by preventing the binding of more robust agonists. An "antagonist" refers to a ligand that binds a membrane protein without stimulating any activity. An "antagonist" is also known as a "blocker" because of its ability to prevent binding of other ligands and, therefore, block agonist-induced activity. Further, an "inverse agonist" refers to an antagonist that, in addition to blocking agonist effects, reduces a membrane proteins' basal or constitutive activity below that of the unliganded protein. Ligands may also be allosteric regulators. "Allosteric regulators" or otherwise "allosteric modulators," "allosteric ligands" or "effector molecules," as used herein, refer to ligands that bind at an allosteric site (that is, a regulatory site physically distinct from the protein's active site) of a membrane protein, in particular a membrane protein such as Vitamin K epoxide reductase. Allosteric modulators are non-competitive because they bind membrane proteins at a different site and modify their function even if the endogenous ligand also is binding. Allosteric regulators that enhance the protein's activity are referred to herein as "allosteric activators" or "positive allosteric modulators," whereas those that decrease the protein's activity are referred to herein as "allosteric inhibitors" or otherwise "negative allosteric modulators."

The disclosure provides engineered cells or cellular systems (cell cultures, host cells, organisms) that can express proteins, particularly membrane proteins, at higher levels either at the cellular surface or in other cell compartments. In particular, the proteins that are expressed by these cells or cellular systems are maintained or stabilized in a particular functional conformation. Further, methods are provided that use such cells or cellular systems to produce these proteins. It will be appreciated that while the disclosure has been exemplified with Vitamin K epoxide reductase, it is equally applicable to any membrane protein, especially a membrane protein that is poorly expressed and has a low stability in a recombinant host cell.

Accordingly, a first aspect of the disclosure relates to a host cell comprising: an exogenous nucleic acid molecule encoding a membrane protein, said membrane protein comprises at least one mutation; and at least one host cell-specific mutation.

The "host cell," according to the disclosure, can be of any prokaryotic organism. According to a preferred embodiment, the host cell is a bacterial cell or bacterium, such as *E. coli*. The nature of the cells used will typically depend on the ease and cost of producing the foreign membrane protein(s), the desired membrane properties, the origin of the target protein, the intended application, or any combination thereof.

By "membrane protein" is understood a protein that is attached to or associated with a membrane of a cell or an organelle. They are often subdivided into several categories including integral membrane proteins, peripheral membrane proteins and lipid-anchored proteins. Preferably, the membrane protein is an integral membrane protein that is permanently bound to the lipid bilayer and which requires a detergent or another apolar solvent to be removed. Integral membrane proteins include transmembrane proteins that are permanently attached to the lipid membrane and span across the membrane one or several times. Examples of suitable membrane proteins include receptors such as G protein couple receptors, growth factor receptors; transmembrane ion channels such as ligand-gated and voltage gated ion channels; transmembrane transporters such as neurotransmitter transporters; enzymes; carrier proteins; ion pumps; viral membrane proteins and supramolecular complexes thereof, amongst others, serotonin and olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, histamine receptors, protease-activated receptors, rhodopsins and other G-protein coupled seven transmembrane segment receptors, CXCR4, GPR3, rhodopsin, vasopressin receptor, β1 adrenergic receptor, β2 adrenergic receptor, β3 adrenergic receptor, al adrenergic receptors and the α2 adrenergic receptor, M1 muscarinic receptor, M2 muscarinic receptor, M3 muscarinic receptor, M4 muscarinic receptor, M5 muscarinic receptor, angiotensin II receptors.

Depending on their intended use, membrane proteins as referred to herein can be of any species, such as fungus (including yeast), nematode, virus, insect, plant, bird (e.g., chicken, turkey), reptile, or mammal (e.g., a mouse, rat, rabbit, hamster, gerbil, dog, cat, goat, pig, cow, horse, whale, monkey, or human).

Notably, fragments or portions, or mutants, variants, or analogues of any of the aforementioned proteins and polypeptides are also included among the suitable proteins, polypeptides and peptides that can be produced by the cells and methods presented herein. In particular, a membrane protein, as used herein, may be any naturally occurring or non-naturally occurring (i.e., altered by man) membrane protein. Within this context, the term "naturally-occurring" means a membrane protein that is naturally produced (for example, and without limitation, by a mammal, more specifically by a human, or by a virus, or by a plant, or by an insect, amongst others). Such membrane proteins are found in nature. Analogously, the term "non-naturally occurring" means a membrane protein that is not naturally produced. Wild-type membrane proteins that have been made constitutively active through mutation, and variants of naturally-occurring membrane proteins are examples of non-naturally occurring membrane proteins. Non-naturally occurring membrane proteins may have an amino acid sequence that is at least 80% identical to, at least 90% identical to, at least 95% identical to or at least 99% identical to, a naturally-occurring membrane protein. Taking the vitamin K epoxide reductase as a particular non-limiting example within the scope of the disclosure, it should be clear from the above that in addition to the human vitamin K epoxide reductase, the rat vitamin K epoxide reductase or other mammalian vitamin K epoxide reductase may also be employed. In addition, the term is intended to encompass wild-type polymorphic variants and certain other active variants from a particular species. For example, a "human vitamin K epoxide reductase" has an amino acid sequence that is at least 80%, 85%, 90%, 92%, 94%, 95%, 96%, 97%, 98%, 99% identical to (e.g., at least 95% or at least 98% identical to) the naturally occurring "human vitamin K epoxide reductase". Further, it will be appreciated that the disclosure also envisages membrane proteins, in particular vitamin K epoxide reductase, with a loop deletion, or an N- and/or C-terminal deletion, or a substitution, or an insertion or addition in relation to its amino acid or nucleotide sequence, or any combination thereof (as defined hereinbefore), or a membrane protein in complex with another chemical entity such as one or more interacting proteins or an agonist/antagonist/inverse agonist.

Thus, according to specific embodiments, the tools and methods for membrane protein expression provided herein can be further combined with known improvements for membrane protein expression that typically involve production of variants. Examples thereof include, but are not limited to, the use of a signal sequence specific to the species of eukaryotic cell used rather than the membrane protein-specific signal sequence, the use of a truncated membrane protein versus the use of an intact protein, the use of a membrane protein with a sequence insertion, and so on. Of course, these different variations can further be combined with each other.

According to still other specific embodiments, more than one, i.e., two or more different proteins may be produced simultaneously. Preferably, at least one of the proteins is a membrane protein. The proteins may all be membrane-bound, all be secreted proteins or a mixture thereof. When more than one protein is produced, care will be taken that they can be recovered easily either separately or together. In a specific embodiment, even higher production is achieved by expressing multiple copies of the protein to be expressed, e.g., as a polyprotein.

Preferably, the produced (membrane) proteins are functional, for instance, the produced receptors remain capable of ligand binding and/or signal transduction.

The host cell, according to the disclosure, is engineered so to express a membrane protein. According to other embodiments, the expression of the membrane proteins in the host cell, as described herein, is preferably regulated by appropriate promoters. The choice of a promoter will typically depend on the nature of the host cell. The choice further depends on the desired temporal expression of a particular protein, as described herein. The proteins may be expressed constitutively or in an inducible way. Accordingly, the promoter may be a constitutive or inducible promoter. The conditions for inducing a promoter may be chosen from the following group of inducing conditions: metabolic, or stress, or pH, or temperature, or drug inducing conditions, or other. Promoters may be derived directly from naturally occurring genes, or may be synthesized to combine regulatory sequences from different promoter regions. Preferably, the promoter is an exogenous promoter that will typically be strong enough to ensure overexpression of the protein(s).

In a preferred embodiment, the promoter is an inducible promoter. Examples of inducible promoters useful for the practice of the disclosure, in particular for bacterial cells, include, without limitation, the isopropyl β-D-thiogalactopyranoside (IPTG)-inducible promoter.

It will be appreciated that having increased stability with respect to structure and/or a particular biological activity of a membrane protein may also be a guide to the stability to other denaturants or denaturing conditions including heat, a detergent, a chaotropic agent and an extreme pH. Other methods to increase the stability of a functional conformational state of a membrane protein under non-physiological conditions can include induction by dilution, concentration, buffer composition, heating, cooling, freezing, detergent, chaotropic agent, pH. In contrast to water-soluble proteins, thermodynamic studies of membrane protein folding and stability have proven to be extremely challenging, and complicated by the difficulty of finding conditions for reversible folding. Unfolding of helical membrane proteins induced by most methods, such as thermal and chemical approaches, is irreversible as reviewed by Stanley and Fleming (2008, Archives of Biochemistry and Biophysics 469:46). The term "thermostabilize," "thermostabilizing," "increasing the thermostability of," as used herein, therefore, refers to the functional rather than to the thermodynamic properties of a membrane protein and to the protein's resistance to irreversible denaturation induced by thermal and/or chemical approaches including, but not limited to, heating, cooling, freezing, chemical denaturants, pH, detergents, salts, additives, proteases or temperature. Irreversible denaturation leads to the irreversible unfolding of the functional conformations of the protein, loss of biological activity and aggregation of the denaturated protein. The term "(thermo)stabilize," "(thermo)stabilizing," "increasing the (thermo)stability of," as used herein, applies to membrane proteins embedded in lipid particles or lipid layers (for example, lipid monolayers, lipid bilayers, and the like) and to membrane proteins that have been solubilized in detergent.

According to particularly envisaged embodiments, cell cultures of host cells of the disclosure are also provided, as well as membrane preparations derived thereof (including the target membrane protein attached to either the cell surface membrane or retained in another subcellular membrane compartment). Membrane preparations include membrane fragments as well as membrane-detergent extracts and can be prepared according to known techniques, for example, as reviewed in detail in Cooper, 2004, J. Mol. Recognit. 17:286, incorporated herein by reference. A membrane preparation is also meant to include any liposomal composition which may comprise natural or synthetic lipids or a combination thereof. Examples of membrane or liposomal compositions include, but are not limited to, organelles, membrane preparations, Virus Like Lipoparticles, lipid layers (bilayers and monolayers), lipid vesicles, high-density lipoparticles (e.g., nanodisks), and the like.

Applications

The host cells, or cell cultures or membrane preparations derived thereof, can be used to produce higher amounts of often poorly expressed and unstable target membrane proteins, optionally stabilized in a particular conformation, either at the cellular surface or in other cell compartments. As such, they are of immediate use as research tool for a wide range of functional and/or structural studies.

Accordingly, in a further aspect, the disclosure provides a method of producing or enhancing the production of a membrane protein in a host cell comprising the steps of: (a) providing a host cell, according to the disclosure, as described hereinbefore, (b) culturing the host cell under conditions suitable for expressing the membrane protein.

During or after the protein production in the host cells, the protein or proteins of interest can be recovered from the cells. Accordingly, the methods of protein production may, optionally, also comprising the step of isolating the expressed protein, either alone, or in complex with a ligand and/or with one or more downstream interacting proteins. This typically involves recovery of the material wherein the protein(s) are present (e.g., a cell lysate or specific fraction thereof, the medium wherein the protein is secreted) and subsequent purification of the protein. Means that may be employed to this end are known to the skilled person and include specific antibodies, tags fused to the proteins, affinity purification columns, and the like.

Other applications are particularly envisaged by making direct use of the host cells or cell cultures, according to the disclosure, or by using membrane preparations derived thereof, which will be described further herein, including compound screening.

In the process of compound screening, lead optimization and drug discovery, there is a requirement for faster, more effective, less expensive and especially information-rich screening assays that provide simultaneous information on various compound characteristics and their effects on various cellular pathways (i.e., efficacy, specificity, toxicity and drug metabolism). Thus, there is a need to quickly and inexpensively screen large numbers of compounds in order to identify new specific ligands of a protein of interest, preferably conformation-selective ligands, which may be potential new drug candidates. The disclosure solves this problem by providing host cells expressing at the cellular surface or in a particular cellular membrane fraction high levels of membrane proteins. Such host cells, as well as host cell cultures or membrane preparations derived thereof, can then be used as immunogens or selection reagents for screening in a variety of contexts. One can quickly and reliably screen for and differentiate between receptor agonists, inverse agonists, antagonists and/or modulators as well as inhibitors of vitamin K epoxide reductase and vitamin K epoxide reductase-dependent pathways, so increasing the likelihood of identifying a ligand with the desired pharmacological properties. Screening performance for disease indications, associated with a particular functional conformer of a target membrane protein will be improved by making use of the host cells of the disclosure.

Thus, according to another embodiment, the disclosure encompasses the use of the host cells, or host cell cultures, or membrane preparations derived thereof, according to the disclosure and as described hereinbefore, in screening and/or identification programs for conformation-selective binding partners of a membrane protein, which ultimately might lead to potential new drug candidates.

According to one embodiment, the disclosure envisages a method of identifying compounds capable of selectively binding to a functional conformational state of a membrane protein, the method comprising the steps of: (i) Providing a host cell or host cell culture or membrane preparation derived thereof, according to the disclosure, harboring a membrane protein in a functional conformational state, and (ii) Providing a test compound, and (iii) Evaluating whether the test compound binds to the functional conformational state of the membrane protein, and (iv) Selecting a compound that selectively binds to the functional conformational state of the membrane protein.

Specific preferences for the host cells, cultures and membrane preparations thereof are as defined above with respect to the first aspect of the disclosure.

Screening assays for drug discovery can be solid phase (e.g., beads, columns, slides, chips or plates) or solution phase assays, e.g., a binding assay, such as radioligand binding assays. In high-throughput assays, it is possible to screen up to several thousand different compounds in a single day in 96-, 384- or 1536-well formats. For example, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. It is possible to assay many plates per day; assay screens for up to about 6.000, 20.000, 50.000 or more different compounds are possible today. Preferably, a screening for membrane protein conformation-specific compounds will be performed starting from host cells, or host cell cultures, or membrane preparations derived thereof.

Various methods may be used to determine binding between the stabilized membrane protein and a test compound, including, for example, enzyme linked immunosorbent assays (ELISA), surface Plasmon resonance assays, chip-based assays, immunocytofluorescence, yeast two-hybrid technology and phage display, which are common practice in the art, for example, in Sambrook et al., 2001, Molecular Cloning, A Laboratory Manual. Third Edition. Cold Spring Harbor Laboratory Press, Cold Spring Harbor, N.Y. Other methods of detecting binding between a test compound and a membrane protein include ultrafiltration with ion spray mass spectroscopy/HPLC methods or other (bio)physical and analytical methods. Fluorescence Energy Resonance Transfer (FRET) methods, for example, well known to those skilled in the art, may also be used. It will be appreciated that a bound test compound can be detected using a unique label or tag associated with the compound, such as a peptide label, a nucleic acid label, a chemical label, a fluorescent label, or a radio frequency tag, as described further herein.

The compounds to be tested can be any small chemical compound, or a macromolecule, such as a protein, a sugar, nucleic acid or lipid. Typically, test compounds will be small chemical compounds, peptides, antibodies or fragments thereof. It will be appreciated that in some instances the test compound may be a library of test compounds. In particular, high-throughput screening assays for therapeutic compounds such as agonists, antagonists or inverse agonists and/or modulators form part of the disclosure. For high-throughput purposes, compound libraries or combinatorial libraries may be used such as allosteric compound libraries, peptide libraries, antibody libraries, fragment-based libraries, synthetic compound libraries, natural compound libraries, phage-display libraries and the like. Methodologies for preparing and screening such libraries are known to those of skill in the art.

The test compound may optionally be covalently or non-covalently linked to a detectable label. Suitable detectable labels and techniques for attaching, using and detecting them will be clear to the skilled person, and include, but are not limited to, any composition detectable by spectroscopic, photochemical, biochemical, immunochemical, electrical, optical or chemical means. Useful labels include magnetic beads (e.g., dynabeads), fluorescent dyes (e.g., all Alexa Fluor dyes, fluorescein isothiocyanate, Texas red, rhodamine, green fluorescent protein and the like), radiolabels (e.g., .sup.3H, .sup.125I, .sup.35S, .sup.14C, or .sup.32P), enzymes (e.g., horse radish peroxidase, alkaline phosphatase), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Other suitable detectable labels were described earlier within the context of the first aspect of the disclosure relating to a binding domain.

Thus, according to specific embodiments, the test compound as used in any of the above screening methods is selected from the group comprising a polypeptide, a peptide, a small molecule, a natural product, a peptidomimetic, a nucleic acid, a lipid, lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or nanobody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, engineered CH2 domains (nanoantibodies), as defined hereinbefore.

It may be desirable to identify and characterize natural or endogenous ligands of target membrane proteins. In particular, there is a need to "de-orphanise" vitamin K epoxide reductase for which a natural activating ligand has not been identified. Such ligands may be recovered from biological samples such as blood or tissue extract or from libraries of ligands. Thus, according to a particular embodiment, the test compound, as used in any of the above screening methods, is provided as a biological sample. In particular, the sample can be any suitable sample taken from an individual. For example, the sample may be a body fluid sample such as blood, serum, plasma, spinal fluid.

In addition to establishing binding to a target membrane protein in a functional conformational state, it will also be desirable to determine the functional effect of a compound on the membrane protein. In particular, the host cells, host cell cultures or membrane preparations derived thereof, as described herein, can be used to screen for compounds and/or to validate hits or leads that modulate (increase or decrease) the biological activity of the membrane protein. The desired modulation in biological activity will depend on the target of choice. Taking a target vitamin K epoxide reductase as an example, the compounds may bind to the target vitamin K epoxide reductase resulting in the modulation (activation or inhibition) of the biological function of the vitamin K epoxide reductase, for example, the downstream receptor signaling. In some embodiments, the inhibitor of vitamin K epoxide reductase is derived from DsbAC33A. In some embodiments, the vitamin K epoxide reductase inhibitor is a peptide, antigen, epitope, or polypeptide derived from DsbAC33A. This modulation of vitamin K epoxide reductase signaling can occur ortho- or allosterically. The compounds may bind to the target vitamin K epoxide reductase so as to activate or increase receptor signaling; or alternatively, so as to decrease or inhibit receptor signaling. The compounds may also bind to the target vitamin K epoxide reductase in such a way that they block off the constitutive activity of the vitamin K epoxide reductase. The compounds may also bind to the target complex in such a way that they mediate allosteric modulation (e.g., bind to the vitamin K epoxide reductase at an allosteric site). In this way, the compounds may modulate the receptor function by binding to different regions in the vitamin K epoxide reductase (e.g., at allosteric sites). The compounds of the disclosure may also bind to the target vitamin K epoxide reductase in such a way that they prolong the duration of the vitamin K epoxide reductase-mediated signaling or that they enhance receptor signaling by increasing receptor-ligand affinity. Further, the compounds may also bind to the target vitamin K epoxide reductase in such a way that they inhibit or enhance the assembly of vitamin K epoxide reductase functional homomers or heteromers. The efficacy of the compounds and/or compositions comprising the same can be tested using any suitable in vitro assay, cell-based assay, in vivo assay and/or animal model known per se, or any combination thereof, depending on the specific disease or disorder involved.

It will be appreciated that the host cells and derivatives thereof, according to the disclosure, may be further engineered and are, thus, particularly useful tools for the development or improvement of cell-based assays. Cell-based assays are critical for assessing the mechanism of action of new biological targets and biological activity of chemical compounds. For example, without the purpose of being limitative, current cell-based assays for vitamin K epoxide reductase include measures of pathway activation or electron transfer processes.

Still another aspect of the disclosure, relates to a kit comprising a host cell or a host cell culture or a membrane preparation, according to the disclosure. The kit may further comprise a combination of reagents such as buffers, molecular tags, vector constructs, reference sample material, as well as a suitable solid supports, and the like. Such a kit may be useful for any of the applications of the disclosure, as described herein. For example, the kit may comprise (a library of) test compounds useful for compound screening applications.

The following examples are intended to promote a further understanding of the disclosure. While the disclosure is described herein, with reference to illustrated embodiments, it should be understood that the disclosure is not limited hereto. Those having ordinary skill in the art and access to the teachings herein will recognize additional modifications and embodiments within the scope thereof. Therefore, the disclosure is limited only by the claims attached herein.

EXAMPLES

Functional overexpression of polytopic membrane proteins, particularly when in a foreign host, is often a challenging task. Factors that negatively affect such processes are poorly understood. Using the mammalian membrane protein Vitamin K epoxide reductase (VKORc1) as a reporter, we describe a genetic selection approach allowing the isolation of *Escherichia coli* mutants capable of functionally expressing this blood-coagulation enzyme. The isolated mutants map to components of membrane protein assembly and protein quality control YidC and HslV. We show that changes in the VKORc1 sequence and in the YidC hydrophilic groove along with the inactivation of HslV promotes VKORc1 activity and dramatically increase its expression level. We hypothesize that such changes correct for mismatches in the membrane topogenic signals between *E. coli* and eukaryotic cells guiding proper membrane integration. Further, the obtained mutants allow the study of VKORc1 reaction mechanisms, inhibition by warfarin and the high-throughput screening for potential anticoagulants.

Materials and Methods:
Strains, Plasmids Media and Growth Conditions:

Strains and plasmids used in this study are listed in Table 2. Strains usually were grown on rich media (NZ-amine) at 37° C. unless otherwise indicated. For experiments testing the activity of β-galactosidase in agar plates, strains were grown on minimal media M63 (M63 salts with 0.2% glucose, 1 μg/mL vitamin B1, 1 mM MgSO4, 65 μg/ml X-Gal). Antibiotics used were at the following the concentrations: carbenicillin, 100 μg/mL, chloramphenicol, 10 μg/mL, kanamycin, 40 μg/mL, spectinomycin, 100 μg/mL; tetracycline, 15 μg/mL. Glucose and L-arabinose were used at a final concentration of 0.2%, and isopropyl β-D-thiogalactopyranoside (IPTG) was used at a final concentrations of 50-300 μM. Strains carrying PR-Orange under a pBAD promoter were grown in NZ media containing 10 μM all-trans retinal and 0.2% arabinose at OD=0.05.

TABLE 2

| Strain | Genotype | Source |
| --- | --- | --- |
| HK295 | F'Δara-714 galU galK (lac)X74 rpsL thi | Laboratory collection |
| HK314 | HK295 ΔdsbA::FRT | Laboratory collection |
| HK320 | HK295 ΔdsbB::FRT | Laboratory collection |
| HK329 | HK295 ΔdsbB::FRT, ΔdsbA::FRT | Laboratory collection |
| HK325 | HK320 (malF-lacZ102, Kan$^r$) | Laboratory collection |
| NK299 | HK295 ΔmenA::FRT | Laboratory collection |
| NK300 | HK320 ΔmenA::FRT | Laboratory collection |
| EcM2.1 | ΔmutS ΔrecA::toic Ts Δbla::Zeor | Gift of George Church (38) |
| FSH238 | HK325 YidC A11T ΔtnaA::CAT | This study |
| FSH229 | HK325 YidCT362I ΔtnaA::CAT | This study |
| FSH240 | HK325 YidC T372I ΔtnaA::CAT | This study |
| FSH227 | HK325 YidC G512S ΔtnaA::CAT | This study |
| EM116 | HK320 ΔmetL::FRT | This study |
| EM201 | HK320 ΔmetL::FRT hslV T163I, MalF-lacZ(Kan$^r$) | This study |
| EM203 | HK320 ΔmetL::FRT hslV C160Y, MalF-lacZ(Kan$^r$) | This study |
| FSH188 | HK320 ΔhslV::Kan | This study |
| FSH193 | HK320 ΔhslV::FRT | This study |
| FSH207 | FSH193Δ hslV::FRT, MalF-lacZ(Kan$^r$) | This study |
| FSH199 | HK320 ΔhslU::Kan | This study |
| EM205 | FSH199 Δ hslU::FRT | This study |
| EM211 | HK320 ΔhslU::FRT, MalF-lacZ(Kan$^r$) | This study |
| FSH282 | HK325 (YidC T362I-CAT) | This study |
| FSH294 | HK325 (YidC T362I, G512S-CAT) | This study |
| FSH296 | HK325 (YidC T362I, T372I-CAT) | This study |
| FSH380 | HK325 (YidC Q429I-CAT) | This study |
| FSH381 | HK325 (YidC T474I-CAT) | This study |
| FSH382 | HK325 (YidC N521I-CAT) | This study |
| FSH383 | HK325 (YidC Q526I-CAT) | This study |
| FSH384 | HK325 (YidC S520I-CAT) | This study |
| FSH385 | HK325 (YidC T362V-CAT) | This study |
| FSH386 | HK325 (YidC T362L-CAT) | This study |
| FSH387 | HK325 (YidC T362A-CAT) | This study |
| FSH388 | HK325 (YidC T362S-CAT) | This study |
| FSH389 | HK325 (YidC R366H-CAT) | This study |
| FSH391 | HK325 (YidC R366I-CAT) | This study |
| ELM93 | HK325 (YidC T362F-CAT) | This study |
| ELM94 | HK325 (YidC T362K-CAT) | This study |
| ELM95 | HK325 (YidC T362E-CAT) | This study |

| Plasmid | Description | Source |
| --- | --- | --- |
| pTrc99a | pBR322 ori Amp$^r$ | Laboratory collection |
| pBAD34 | pACYC184 ori Cm$^r$ | Laboratory collection |
| pBAD43 | pSC101 ori Spec$^r$ | Laboratory collection |

TABLE 2-continued

| | | |
|---|---|---|
| pBAD100 | pACYC184 ori Spec<sup>r</sup> | This study |
| pELM6 | pBAD100 E. coli YidC | This study |
| pJBL420 | pTrc99a rat VKORc1 | This study |
| pJBL420.1 | pTrc99a rat VKORc1 ΔA31AR | This study |
| pEM101 | pTrc99a rat VKORc1 ΔA31AR G60D | This study |
| pJBL420.3 | pTrc99a rat VKORc1 ΔA31AR R58H | This study |
| pJBL420.4 | pJBL420 C16A | This study |
| pJBL420.5 | pJBL420 C43A | This study |
| pJBL420.6 | pJBL420 C51A | This study |
| pJBL420.7 | pJBL420 C51A | This study |
| pJBL420.8 | pJBL420 C85A | This study |
| pJBL420.9 | pJBL420 C96A | This study |
| pJBL420.10 | pJBL420 C132A | This study |
| pJBL420.11 | pJBL420 C135A | This study |
| pJBL420.12 | pJBL420-1 C16A | This study |
| pJBL420.13 | pJBL420-1 C43A | This study |
| pJBL420.14 | pJBL420-1 C51A | This study |
| pJBL420.15 | pJBL420-1 C51A | This study |
| pJBL420.16 | pJBL420-1 C85A | This study |
| pJBL420.17 | pJBL420-1 C96A | This study |
| pJBL420.18 | pJBL420-1 C132A | This study |
| pJBL420.19 | pJBL420-1 C135A | This study |
| pFH420 | pTrc99a rat VKORc1-linker (GTGGGSGGGSGS) (SEQ ID NO: 1) - T7 tag | This study |
| pFH421 | pTrc99a rat VKORc1 ΔA31AR-linker-T7 tag | This study |
| pFH422 | pTrc99a rat VKORc1 ΔA31AR G60D-linker-T7 tag | This study |
| pFH436 | pTrc99a rat VKORc1 C16A ΔA31AR G60D C85A C96A-linker-T7 tag | This study |
| pFH437 | pTrc99a rat VKORc1 C16A C43 ΔA31AR G60D C85A C96A-linker-T7 tag | This study |
| pFH438 | pTrc99a rat VKORc1 C16A C51A ΔA31AR G60D C85A C96A-linker-T7 tag | This study |
| pFH439 | pTrc99a rat VKORc1 C16A ΔA31AR G60D C85A C96A C132A-linker-T7 tag | This study |
| pFH440 | pTrc99a rat VKORc1 C16A C51A ΔA31AR G60D C85A C96A C132A-linker-T7 tag | This study |
| pFH441 | pBAD43 E. coli DsbA-FLAG | This study |
| pFH442 | pFH441 C33A-FLAG | This study |
| pFH443 | pTrc99a E. coli YidC | This study |
| pFH444 | pTrc99a E. coli MalF-DsbB | This study, (26) |
| pFH445 | pTrc99a MalF-DsbBK68N | This study, (26) |
| pFH446 | pTrc99a MalF-DsbB K68N, R72N | This study, (26). |

VKORc1 Library and Chromosomal Selection:

pTrc99a carrying human or rat VKORc1 was transformed into XL1-red according to manufacturer's instructions. After 4 cycles of mutagenesis, plasmids libraries (ca. 5*10$^5$ members/library) were extracted from cells and electroporated into electrocompetent HK325 and tested for motility. Motile flares were streaked twice and then retested for motility in the presence or absence of low concentration of IPTG±warfarin. Plasmids were isolated from the motile strains, transformed into HK325, and tested again for motility.

For chromosomal mutagenesis, HK325 or FSH230 carrying pTrc99a with rat VKORc1 genes (wt or the three amino acid deletion A31AR) was treated with EMS according to Miller (36). Briefly, culture at mid-log phase was harvested and washed twice with equal volume of buffer A (1× per liter, 4.5 g of $KH_2PO_4$, 10.5 g of $K_2HPO_4$, 1 g $(NH_4)_2SO_4$, and 0.5 g sodium citrate.$2H_2O$). Cells were pelleted and resuspended in half the original volume of buffer A. Subsequently, 30 μl of the mutagen ethyl methanesulfonate (EMS) was added to 2 ml samples of culture and incubated at 37° C. for 15, 30, 60, 90 and 120 min with aeration. Cells were pelletted again, washed of EMS and outgrown for 4 hours in NZ media. Finally, the cultures were spun down, NZ media aspirated and the pelleted cells resuspend in M63 buffer before plating on M63 glucose agar containing 8-10 mM TCEP. Colonies that started to appear after 24 hours after incubation at 37° C. were restreaked on similar plates and subsequently tested for motility and for white color on a minimal media plate containing X-gal.

Strains Construction and Chromosomal Site-Directed Mutagenesis:

Moving alleles between strains were done using standard P1 transduction. Spontaneous loss of plasmids carrying potentially functional VKORc1 was sought by growing the strain on M63 media in the presence of IPTG and X-gal and the absence of antibiotic selection. The appearance of blue colonies was indicative of plasmid loss, which was verified by streaking on plates containing carbenicillin. yidC mutants were moved into the parental strain HK325 by first introducing into the yidC mutant strains a chloramphenicol antibiotic resistance cassette (CAT) in place of tnaA, which is tightly linked to yidC, essentially as described in Datsenko and Wanner (37). P1 was then used to transduce the yidC mutation into HK325 by its linkage to chloramphenicol resistance. Signal or double point mutants in the chromosomal locus of yidC were made by allele replacement as follows. We first made a DNA fragment of portions of yidC operon (by gene synthesis or PCR) carrying the intended nucleotide substitution. Subsequently, we made a fusion at the 3' end of this yidC DNA fragment and a CAT cassette by Gibson assembly. After PCR amplification of this DNA fusion, the resultant product was electroporated into HK325 carrying pKD46 and selected for chloramphenicol resistant colonies. At first attempt, none of the 20 colonies we screened had the intended yidC mutation, even though they all had the CAT cassette fused to yidC operon as designed. Presumably the DNA base-pair repair system had repaired the point mutation. Therefore we utilized a ΔmutS, ΔrecA strain (EcM2.1, George Church). This strain is impaired in homologous recombination and in base-pair mismatch correction and carries heat-inducible lambda red genes on the chromosome. We first introduced the yidC::CAT PCR fragment into EcM2.1 containing a plasmid coding for yidC$_{wt}$, confirmed the nucleotide substitution by sequencing, and then transduced the chromosomal yidC::CAT allies using P1 into HK325, containing a plasmid coding for yidC$_{wt}$ or an empty plasmid. The essentiality or the lethality of a particular amino substitution was assessed by examining the transduction efficiency. In general, lethal mutations have 50 times less transductants in HK325 containing empty plasmid. All mutations were finally confirmed by sequencing.

Construction of double mutants using hsIV point mutants Cys160Tyr and Thr163Ile in a clean background was as follows. metL is required for the biosynthesis of aspartate and thus ΔmetL cannot grow on minimal medium. HK320 was made metL⁻ by P1 transduction of metL::KAN from JW3911 and KAN cassette was removed by pCP20 giving EM116. P1 was grown on strains baring hsIV mutations Cys160Tyr and Thr163Ile then used to transuce EM116 selecting on minimal plates to give EM203 and EM201. Finally, yidC$_{T362I}$ was moved from FSH229 to EM203 by P1 transduction selecting on chloramphenicol. The mutations were confirmed by sequencing. Clean deletions of hsIV and hsIU were introduced by P1 transduction into HK320 from the Kieo collection strains JW3903 and JW3902, respectively. Then Kan cassette was removed by pCP20 before transducing the MalF-lacZ(Kan$^r$) to give FSH207 (ΔhsIV) and EM211 (ΔhsIU).

Motility and β-galactosidase Activity:

Bacterial motility was assayed by stabbing a colony into 0.3% minimal medium Agar plates containing M63 salts, 0.2% Glucose, IPTG, and carbenicillin. Motility was examined after two days of growth at 30 C. When using arabinose to induce expression from pBAD promoter, 0.5% glycerol was used instead of glucose in addition to 0.1% NZ to enhance motility.

Strains were grown at 37° C. in NZ media overnight from a single colony. Next day, the overnight culture was diluted 1:100 into a fresh media containing appropriate concentration of IPTG and grown until the OD600 reached 1. Cells were collected by centrifugation and resuspended in lysis buffer to give a calculated OD600 of 5. The lysis buffer is composed of 20 mM phosphate (pH7.0), 1× of PopCulture® (Novagen), lysozyme and Benzonase® (Millipore). Twenty microliter of the lysate was used to assay β-galactosidase activity in a total volume of 200 µl of reaction buffer (36).

Engineering of PR-Orange:

PR-Orange was identified by fluorescence-based screening of large libraries of PR variants expressed in colonies of E. coli. An identical screen has been used to identify improved archaerhodopsin-based fluorescent indicators of neuronal membrane potential (39). Briefly, libraries of PR-Orange variants were assembled by a two-part overlap extension PCR. The 5' piece used in the overlap extension was prepared by error-prone PCR amplification of the template PROPS, a previously reported fluorescent indicator of membrane potential in E. coli (40). The 3' piece was prepared by high-fidelity PCR amplification of the fluorescent protein mOrange2 (41). The libraries were expressed in the context of E. coli colonies, and those colonies with the highest ratio of PR fluorescence (~700 nm) to mOrange2 fluorescence (~560 nm) were picked and used to inoculate fresh liquid cultures. Following overnight culture, bacteria were lysed and fluorescent brightness was quantified with a microplate reader. The brightest variants were used as templates for the subsequent round of mutagenesis, DNA shuffling by StEP PCR (42), and fluorescence-based screening. After several iterative rounds of screening, we identified PR-Orange with 6 mutations relative to wild-type PR (S65F/D97N/I106V/E165V/N176D/I192N) and substantially improved fluorescence brightness.

Example 1

Mutations in the Rat VKORc1 Gene that Enhance its Expression in a Form Functional in E. coli Disulfide Bond Formation The bacterial proteins DsbB and VKOR and the mammalian protein VKORc1 are polytopic membrane proteins that perform quite analogous electron transfer processes. They all receive electrons from thioredoxin-like proteins and transfer those electrons to membrane-localized quinones (11).

Given these similarities between the proteins and the finding that MtbVKOR can replace DsbB in E. coli, we asked whether rat or human VKORc1, which share 82% sequence identity, could also replace DsbB. However, when these mammalian proteins were expressed in E. coli by even a strong promoter, neither VKORc1 was able to substitute for DsbB. We then considered that efficient expression might be achieved by directly selecting for mutants of the VKORc1s that allowed the proteins to be functional in disulfide bond formation. There are multiple phenotypes conferred on the cell by disulfide bond formation that allow probing by various in vivo assays. Thus, we considered that it might be possible to screen for mutants in which VKORc1 functionally replaces E. coli DsbB either by enhanced expression or functionality. In order to seek such mutants, we mutagenized plasmids carrying rat or human VKORc1 expressed from an isopropyl β-D-thiogalactopyranoside (IPTG)-inducible promoter by several cycles of transformation in the mutator strain XL1-Red. The mutagenized plasmid libraries were then transformed into a ΔdsbB strain selecting for functional VKORc1 clones as indicated by restoration of bacterial motility. A ΔdsbB strain is not motile due to the absence of an essential structural disulfide bond in FlgI, a major component of the flagella machinery. Strains carrying the mutagenized plasmids were screened for motility by spotting dilutions of cultures on a soft agar plate and looking for motile flares that moved out from the culture spotted. The bacteria in the flares were purified, motility confirmed and the mutant strains tested for whether the motility was sensitive to warfarin, a known inhibitor of VKORc1. We obtained 11 mutations in the VKORc1 gene which conferred various degrees of motility (Table 1). Notably, one showing the strongest motility was a deletion of amino acids 31-33 (AAR), denoted rat VKORc1$_{\Delta AAR}$ hereafter. These amino acids according to sequence-based algorithms for predicting membrane topology are in a hydrophilic loop that follows the first TMH and would be located in the bacterial periplasm.

Table 1: Activating mutations in VKORc1. Mutations in Human (Hs) or Rat (Rn) VKORc1$_{wt}$ conferring disulfide bond formation activity in E. coli ΔdsbB are obtained by means of plasmid libraries or EMS mutagenesis. Additional mutations with increased activity are subsequently isolated when starting with a strain carrying a mutation with weak activity (i.e. RnVKORc1$_{\Delta AAR}$ or RnVKORc1$_{R58H}$). Almost all of the mutations obtained are located between amino acid 29 and 80 which, according to some membrane topology prediction algorithms (POLYPHOBIUS and SPOCTOPUS (34-35)), are flanked by the first and second transmembrane helices. The vast majority of the obtained substitutions involve the removal of a positively charged amino acid, or the introduction of a negatively charged one.

TABLE 1

| Mutation | HsVKORc1$_{wt}$ | RnVKORc1$_{wt}$ | RnVKORc1$_{\Delta 31AR}$ | RnVKORc1$_{R58H}$ |
|---|---|---|---|---|
| V29E | 1 | | | |
| V29K → E | | 2 | | |
| ΔA31AR | | 8 | | |
| R33P | | | | 34 |
| A48S | | | 1 | |
| R53H | | | 7 | |
| F55S | 1 | 1 | | 6 |

TABLE 1-continued

| Mutation | HsVKORc1$_{wt}$ | RnVKORc1$_{wt}$ | RnVKORc1$_{\Delta 31AR}$ | RnVKORc1$_{R58H}$ |
|---|---|---|---|---|
| S57P | | | | 7 |
| S57F | | 6 | | |
| R58H | | | 9 | |
| G60D | | 45 | 7 | |
| S52N/G60D | | 1 | | |
| R61H | | | 18 | |
| G62D | 3 | 16 | 2 | |
| G64D | | 1 | 8 | |
| T4I/G64D | | | | 18 |
| G60D/G62D | | 1 | | |
| L65P | | 4 | | |
| N80D | | | 2 | |
| T137P | | 1 | | |

Figure 5:
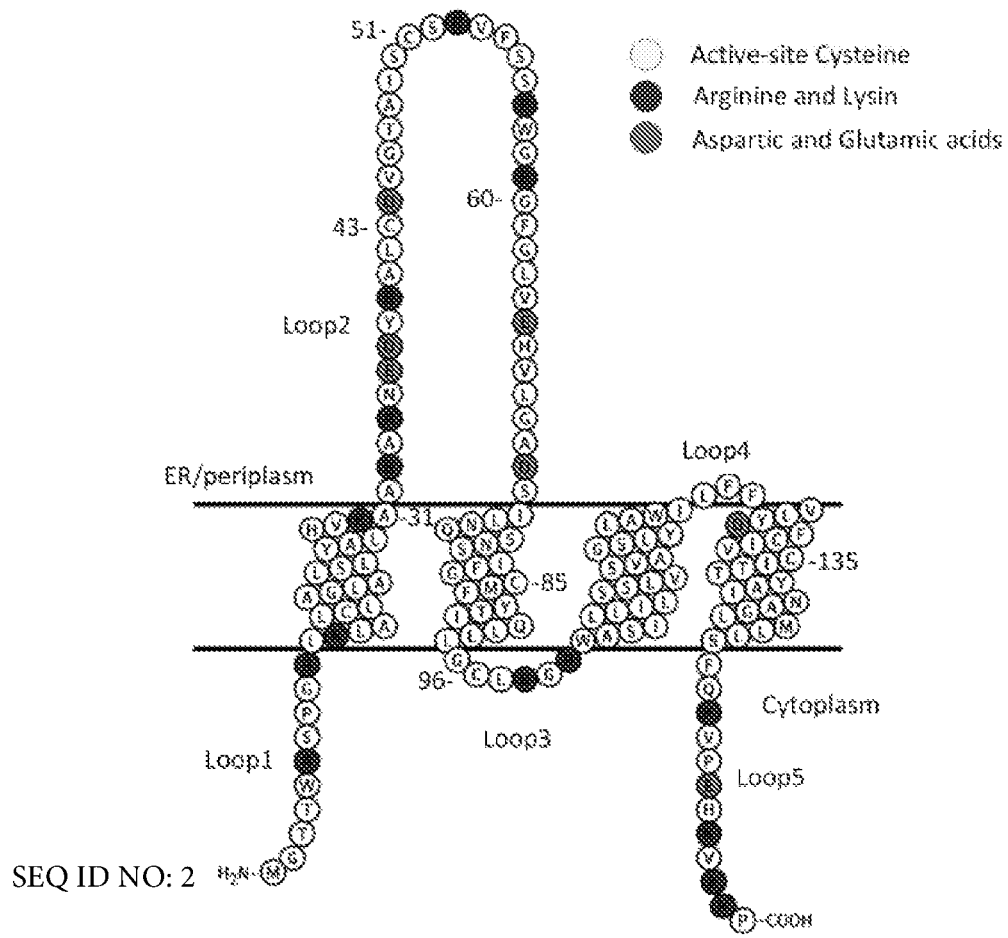
FIG. 5 shows schematics of proposed topology of rat VKORc1 and localization of charged amino acids and active site cysteines. Drawings were done using Proffer (43). Figure discloses SEQ ID NO: 2.

When some of the motile mutants were further mutagenized and screened for secondary mutations that caused even greater motility, 9 additional point mutations were obtained. Remarkably, the vast majority of the amino acid substitutions are located in the loop connecting the first and second predicted TMHs, and involved either the removal of a positively charged amino acid as does VKORc1$_{\Delta AAR}$ or the introduction of a negatively charged one (Materials and Methods (below), FIG. 5 and Table 1). The subcellular localization of this loop of VKORc1, as well as the number of TMH have been controversial (15-17). However, in MtbVKOR this loop contains a pair of redox-active cysteines, and by comparison with the cysteines of DsbB and MtbVKOR, would have to be facing the periplasm for the protein to functionally replace DsbB.

Figure 2:
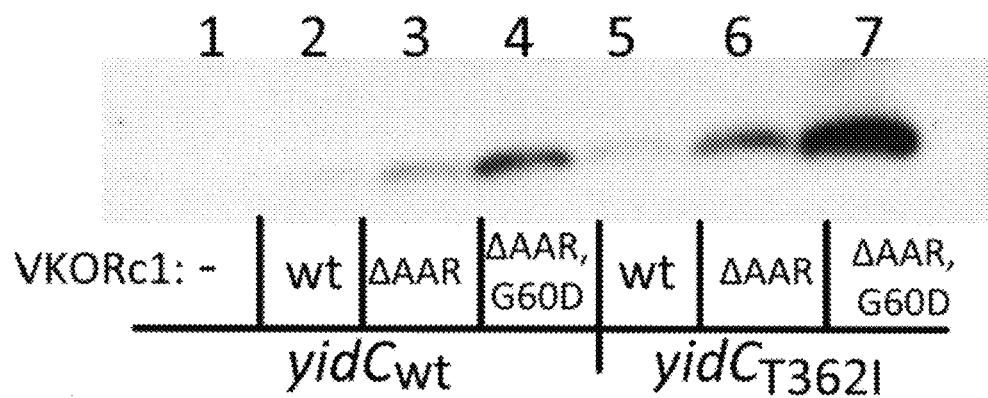
FIG. 2 contains four panels, A-D, showing mutations in VKORc1 alone or in combination with *E. coli* yidClhsIVU mutations confer increased expression and functionality in disulfide bond formation of VKORc1. All strains except for the one with DsbB$^+$ indicated are deleted for dsbB. VKORc1$_{wt}$ is not expressed in *E. coli* unless changes are made to its sequence and to YidC. The expression level Panel (A) and disulfide bond formation activity of VKORc1 (Panels B and C) are dramatically enhanced (low β-galactosidase activity) upon combining these mutations. Panel D depicts HslV$_{C160Y}$ and HslV$_{T163I}$ or the deletion of either component of the HslVU protease complex enables the functional expression of VKORc1$_{AAAR}$ in ΔdsbB. β-galactosidase measurements data are ±SEM (n≥3).
Figure 2:
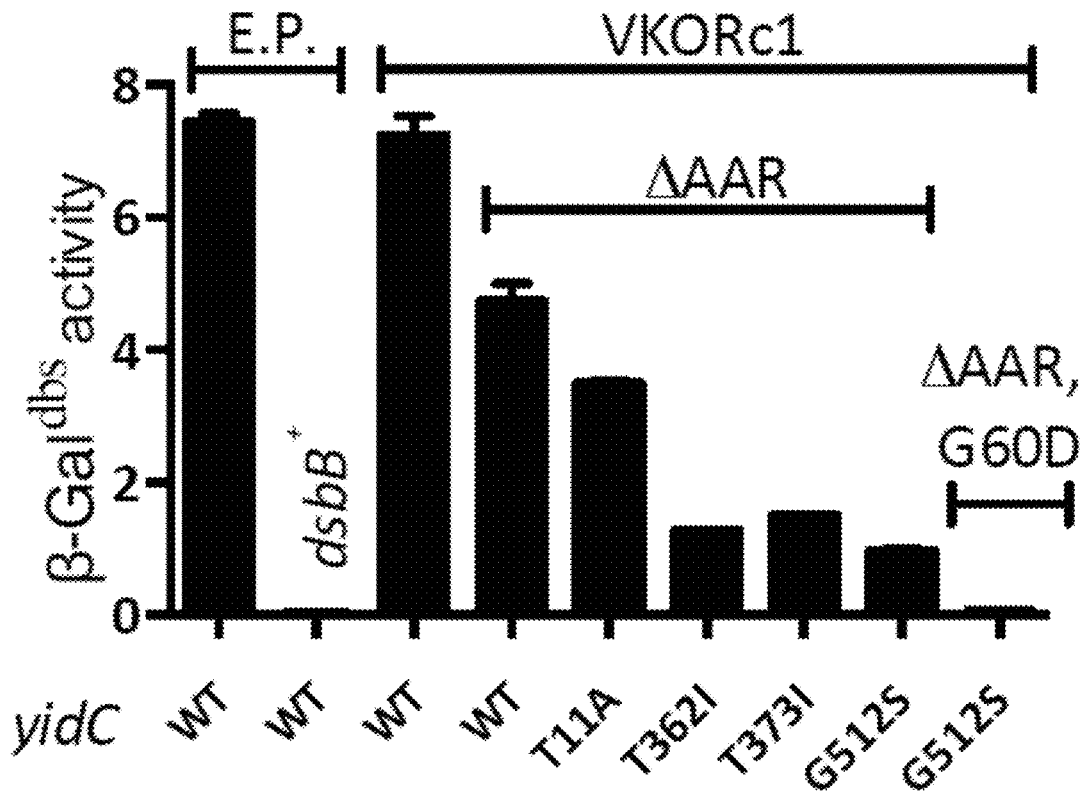
Figure 2:
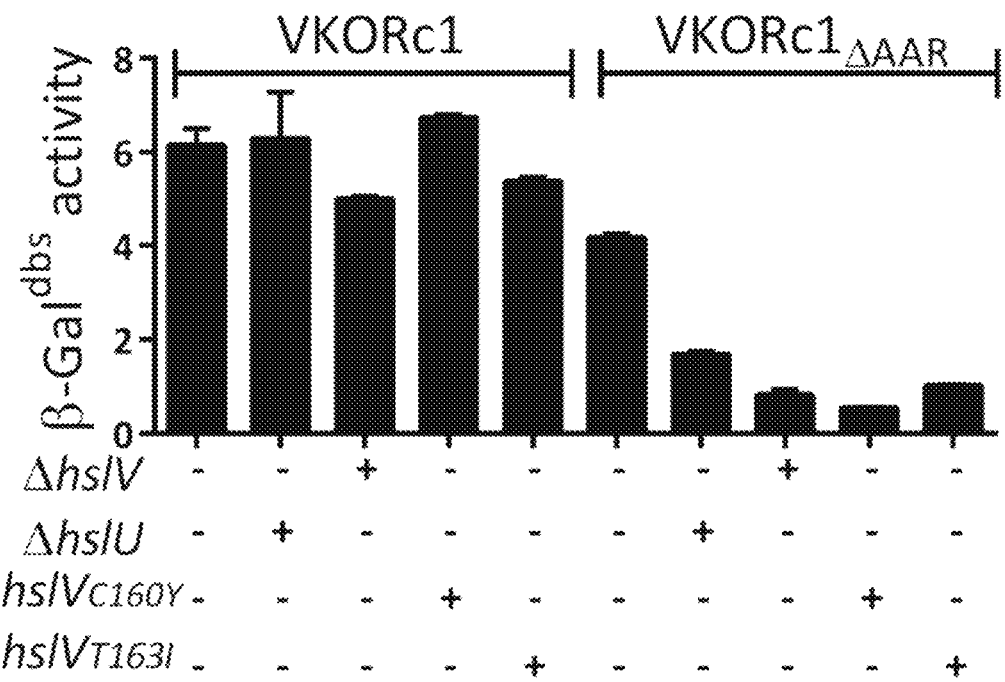
Figure 2:
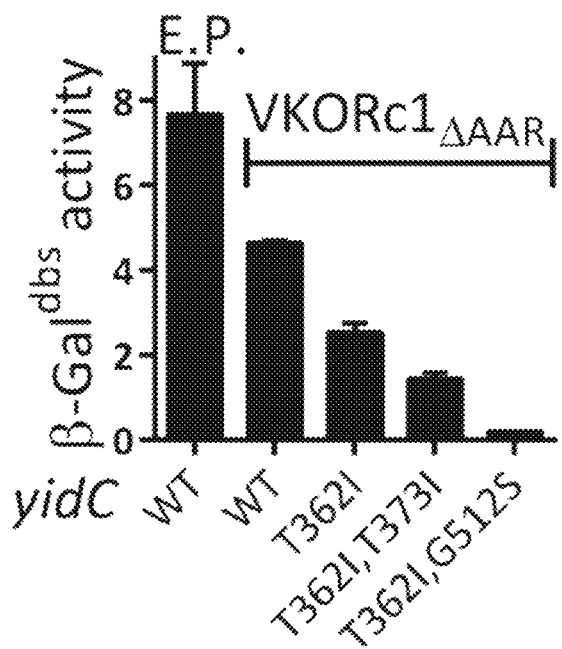
Figure 3:
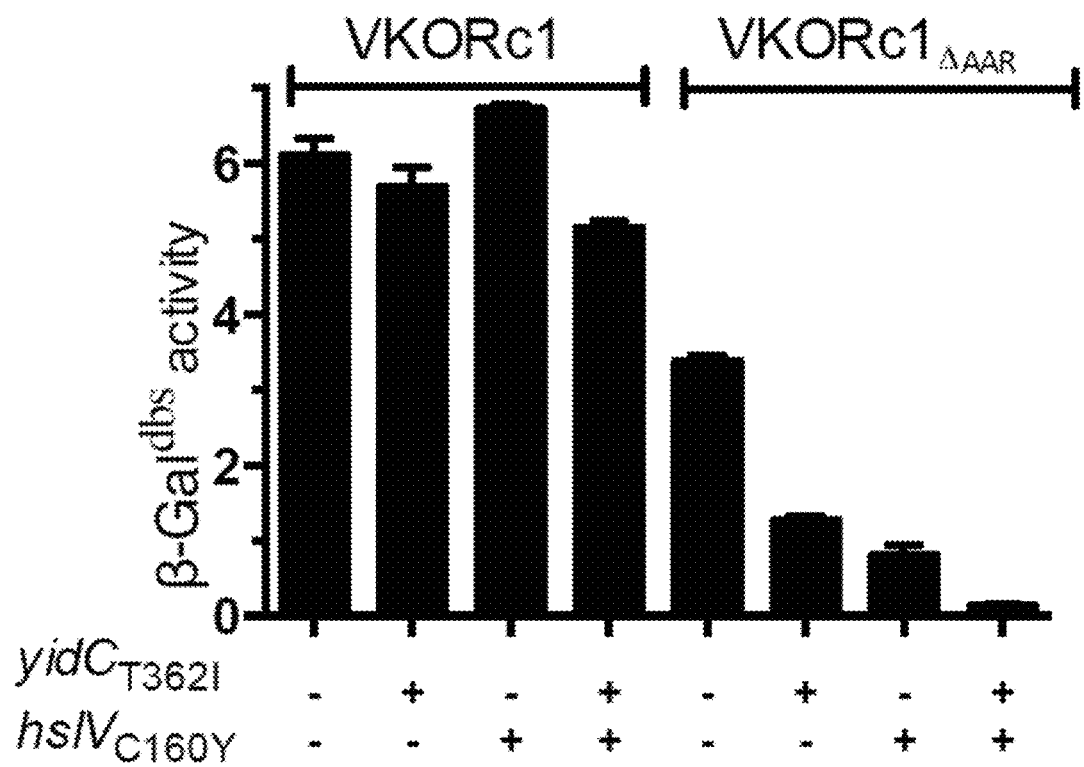
FIG. 3 contains two panels, A and B, showing YidC$_{T362I}$ and HslV$_{C160Y}$ display synergy in increasing functional expression of VKORc1. Panel A depicts β-galactosidase activity in HK325 (yidC$_{wt}$), FSH229 (yidC$_{T362I}$), EM190 (hslV$_{C160Y}$) or FSH231 (yidC$_{T362I}$, hslV$_{C160Y}$)) expressing rat VKORc1$_{wt}$ (pJK420) and VKORc1$_{AAAR}$ (pJLB420.1). Data are ±SEM (n≥3). Panel B depicts expression level of VKORc1$_{wt}$ is dramatically enhanced when expressed in hslV$_{C160Y}$.
Figure 3:
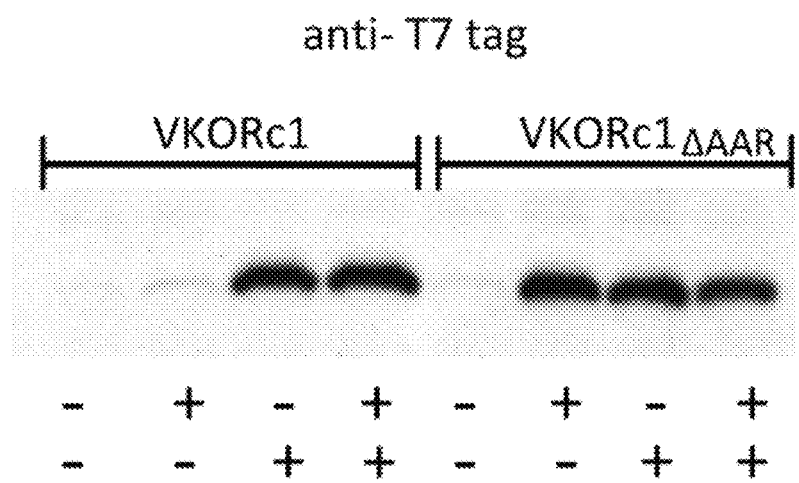
Figure 4:
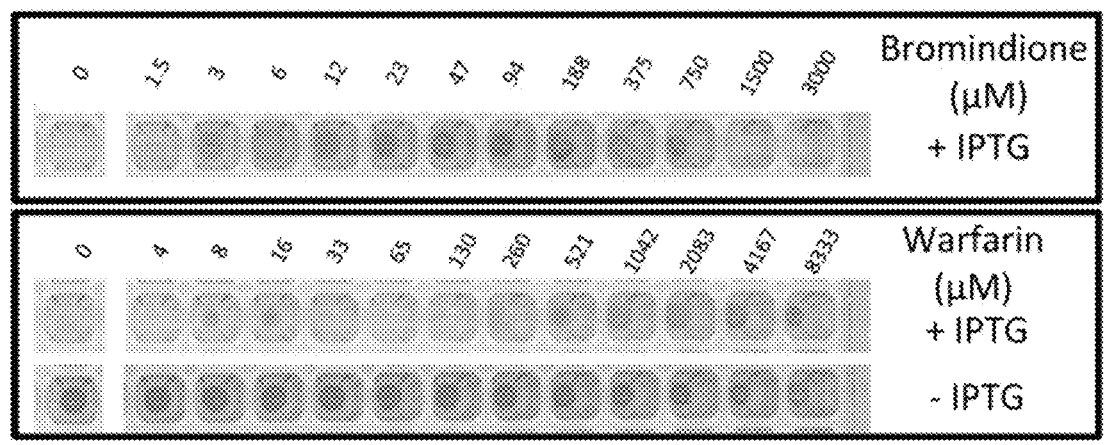
FIG. 4 contains three panels, A-C, showing rat VKORc1 expressed in *E. coli* is inhibited by the anticoagulants bromindione and warfarin. It also interacts in the periplasm with DsbA and with DsbA$_{C33A}$, the latter interaction displaying a dominant negative phenotype, inhibiting VKORc1 activity. Panel A depicts VKORc1 inhibition is described in Materials and Methods (below). Panel B depicts low agar motility plates of FSH231 co-transformed with pTrc99a (empty or carrying VKORc1$_{AAAR,G60D}$) and pBAD43 (empty or carrying DsbA/DsbA$_{C33A}$). Panel C depicts DsbA forms a mixed disulfide with VKORc1 in *E. coli*. Immunoblots of cultures of FSH231 carrying plasmids of VKORc1$_{AAAR,G60D}$ and DsbA cysteine mutants (Materials and Methods (below)). DsbA$_{C33A}$ forms mixed-disulfide with itself as well with several *E. coli* proteins (black stars). T7 tag antibody reacts weakly but non-specifically with some *E. coli* proteins (black asterisks).
Figure 4:
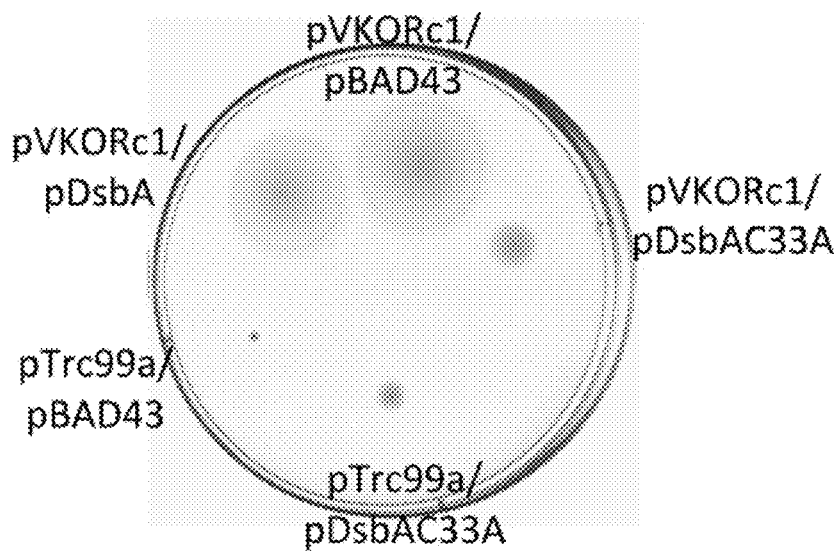
Figure 4:
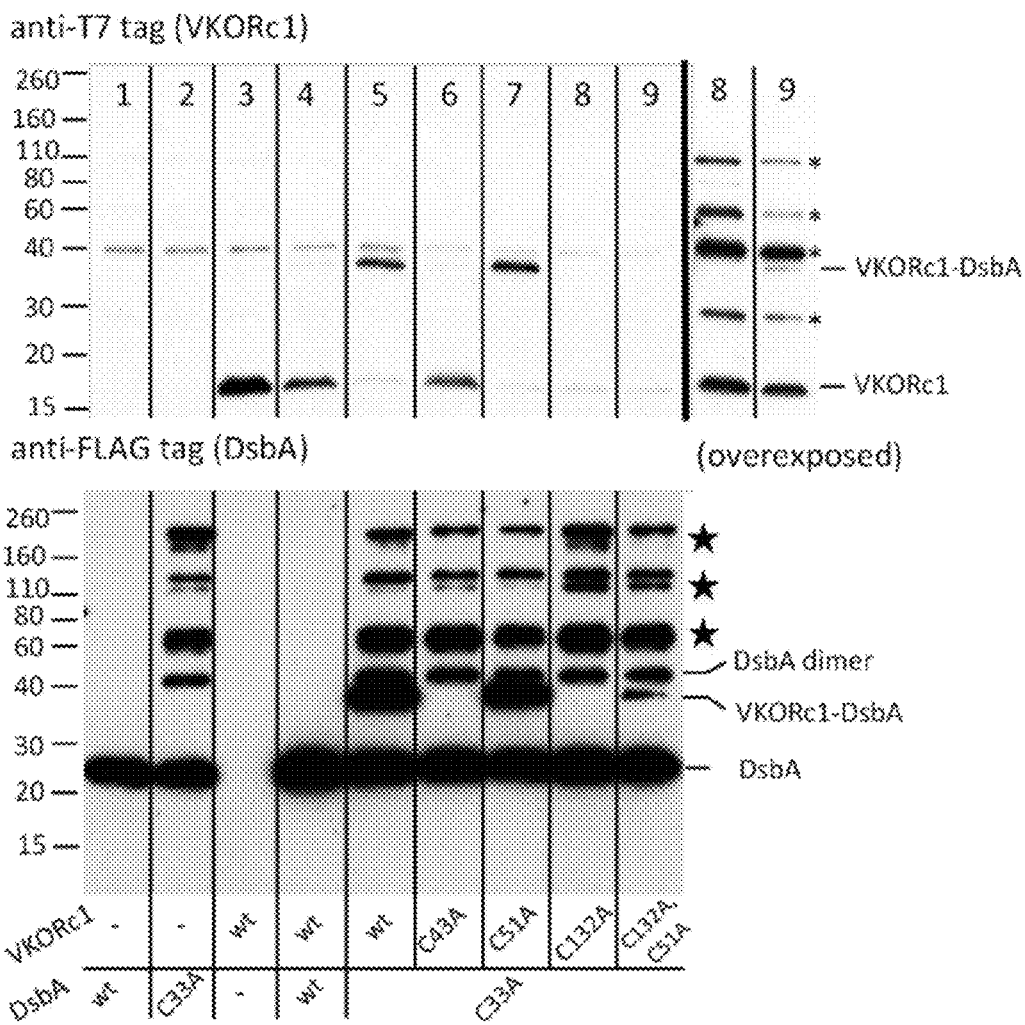

These findings raised the possibility that the native VKORc1s may not assemble properly in the bacterial cytoplasmic membrane because of violations of the positive-inside rule preventing their ability to replace the absent DsbB. The mutations in VKORc1 may have restored an appropriate charge balance across the membrane, thus promoting proper assembly, stability and functional expression. Indeed, Western blot analysis shows that while the wild-type VKORc1 (VKORc1$_{wt}$) is barely expressed, the mutations have a positive and additive effect on amount of protein (FIG. 2, Panel A, compare gel lanes 2, 3 and 4). These findings suggest that VKORc1$_{wt}$ may not assemble properly in the E. coli membrane leading to instability and subsequent degradation.

Example 2

Isolation of Chromosomal Mutations Enhancing VKORc1 Expression

Since the degree of functionality of VKORc1 in disulfide bond formation made possible by the mutations in VKORc1 was still only partial as indicated by weak restoration of E. coli motility, we sought chromosomal mutations in the host E. coli that would increase its functional expression. We devised the following selection and screening strategy: First, we constructed a ΔdsbB strain carrying a plasmid encoding either rat VKORc1$_{wt}$ or the VKORc1$_{\Delta AAR}$ variant. To provide a highly sensitive indicator of disulfide bond formation, this strain (HK325) also expressed a disulfide bond-sensitive version of the enzyme β-galactosidase, β-Gal$^{dbs}$. β-Gal$^{dbs}$ is the product of a fusion between the malF and lacZ genes which expresses a galactosidase exported to the periplasm by translocation signals in the membrane protein MalF. Disulfide bond formation inactivates β-Gal$^{dbs}$ (18). As a result, on agar media containing 5-bromo-4-chloro-3-indolyl-β-D-galactopyranoside (X-Gal), strains that do not make disulfide bonds form blue colonies and those that are highly active in making disulfide bonds form white colonies. This strain was treated with the mutagen Ethyl methanesulfonate (EMS). Since ΔdsbB is unable to grow in the presence of disulfide breaking agents, the mutagenized strain is plated on minimal media agar containing such an agent, tris 2-carboxyethyl phosphine (TCEP), at a concentration sufficient to prevent growth. Colonies that survive on TCEP-containing agar are picked and screened for motility and for white colonies on X-Gal plates, indicating sufficient disulfide bond formation to inactivate β-Gal$^{dbs}$. Blue colonies represent strains that restore disulfide bond formation not at all or very weakly.

We saw immediately that a mutagenized strain expressing the VKORc1$_{wt}$ did not yield colonies that survived the TCEP selection, but a strain carrying the slightly active VKORc1$_{\Delta AAR}$ did. Next, we sequenced the VKORc1$_{\Delta AAR}$ gene of the plasmid from these mutant TCEP survivors, finding that only two of the 20 mutants contained altered VKORc1$_{\Delta AAR}$. These encoded an amino acid substitution G60D previously isolated in our (motility) screen for mutations activating VKORc1$_{wt}$. Then, assuming that at least some of the remaining strains contained chromosomal mutations influencing VKORc1$_{\Delta AAR}$ functional expression, we sequenced the genomic DNA of these strains on an Illumina platform. The eleven candidate strains displaying high levels of VKORc1$_{\Delta AAR}$ carried between 5 and 40 new mutations as a result of EMS treatment. Notably, seven strains contained missense mutations in the gene encoding the insertase yidC, two had mutations in the gene encoding the cytoplasmic protease hsIV and one had missense mutations in genes for biosynthesis of ubiquinone and menaquinone (ubiC, ubiE and menA), molecules involved in disulfide bond formation.

Example 3

Synergy of YidC and HslV Mutations in Facilitating Functional Expression of VKORc1

To confirm that the mutations in yidC alone are sufficient to enhance VKORc1$_{\Delta AAR}$ functional assembly, we introduced these mutations by P1 transduction into the parental strain HK325 and tested for disulfide bond formation activity as judged by inactivation of β-Gal$^{dbs}$ (FIG. 2, Panel B). All of the strains with the transduced yidC mutations, except that which carried yidC$_{A111T}$, showed significantly increased VKORc1 activity as judged by increased resistance to TCEP and diminished activity of the β-galactosidase reporter.

Figure 6:
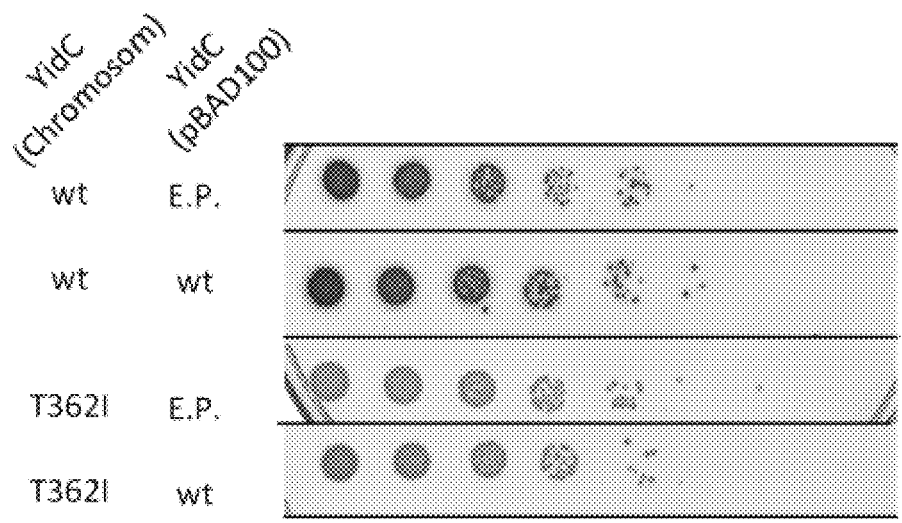
FIG. 6 shows recessive nature of YidC$_{T362I}$: The gain-of-function of VKORc1$_{AAAR}$ in the yidC$_{T362I}$ strain (white color colonies) is diminished in the presence of an additional copy of wild-type (wt) yidC expressed from a plasmid (faint blue colonies). Serial dilutions of a yidC$_{wt}$ strain (HK325) and a yidC$_{T362I}$ strain (FSH229) transformed with VKORc1$_{AAAR}$ and pBAD100, empty (E.P.) or carrying yidC$_{wt}$, are spotted on rich media agar containing X-gal, 0.2% maltose and 300 µM IPTG.
Figure 7:
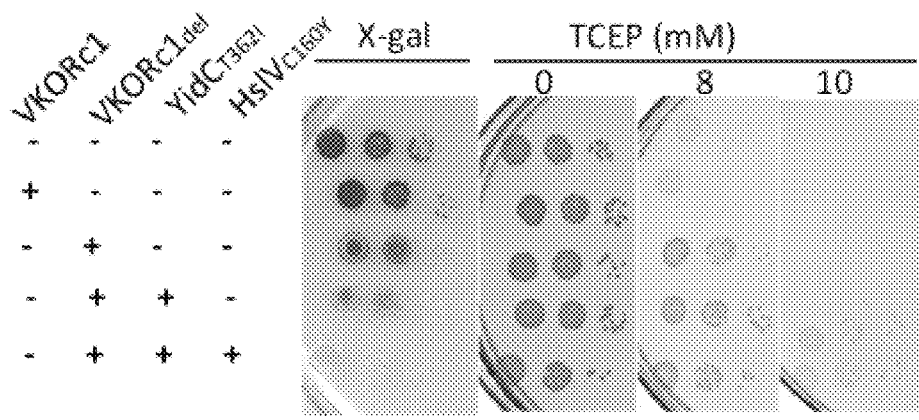
FIG. 7 shows the combination of hslV$^-$ with yidC$_{T362I}$ greatly increases the activity of VKORc1$_{AAAR}$ but not VKORc1$_{wt}$.
Figure 8:
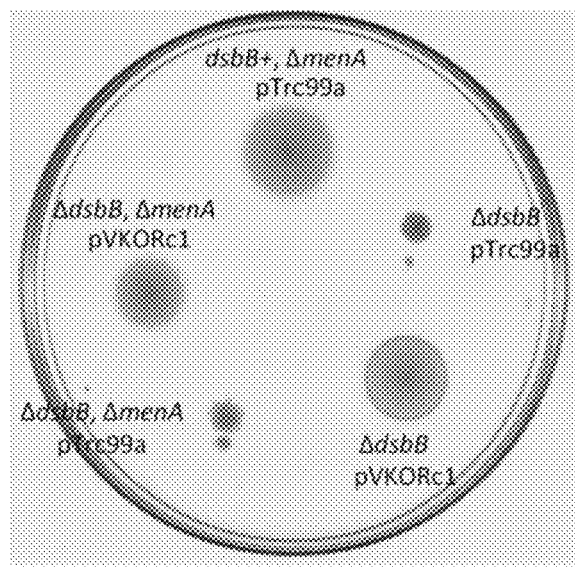
FIG. 8 shows rat VKORc1 is functional in *E. coli* ΔdsbB ΔmenA. Strains transformed with empty pTrc99a plasmid or carrying rat VKORc1 (pVKORc1$_{AAAR, G60D}$) were stabbed into M63 motility agar supplemented with 0.1% NZ amines and grown overnight at 30° C.
Figure 9:
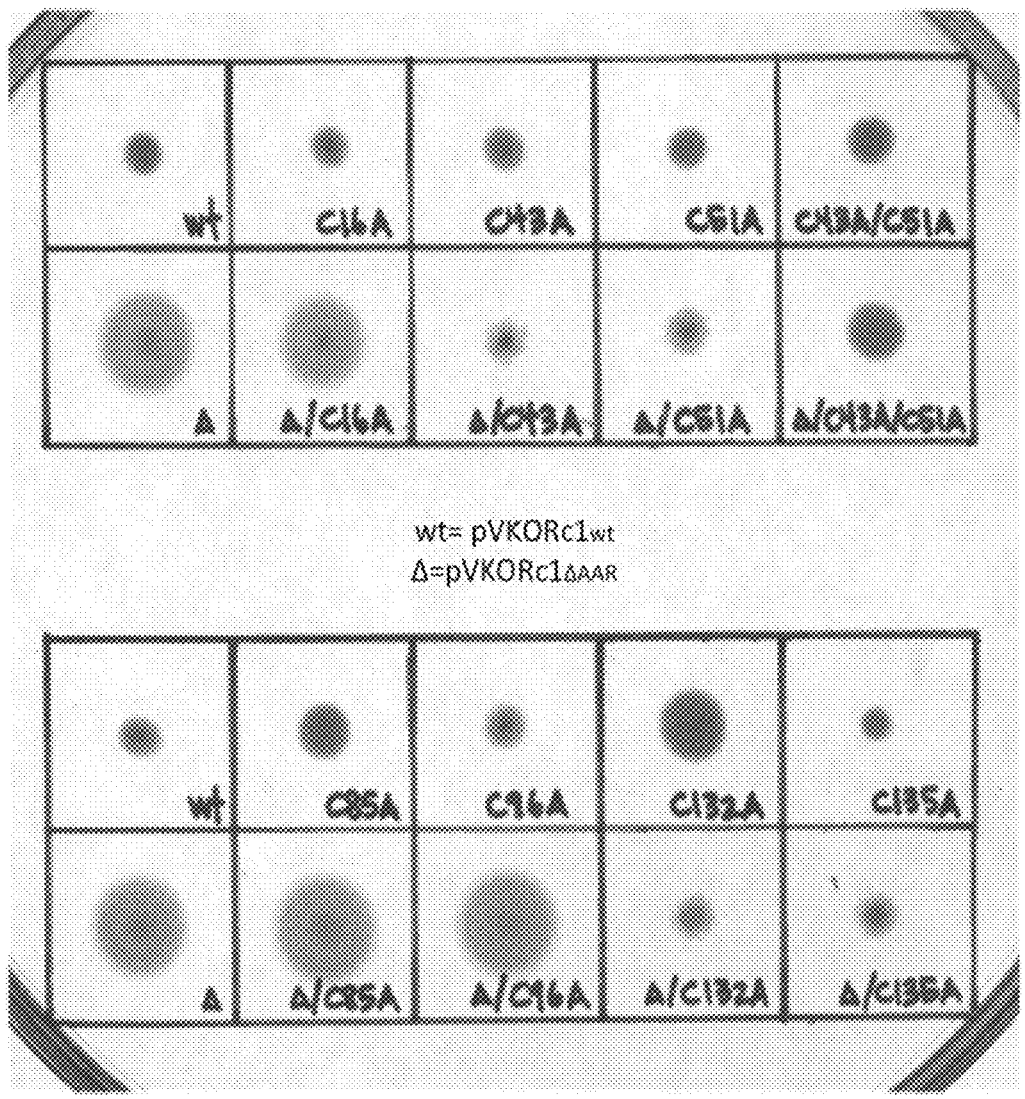
FIG. 9 shows four of the seven cysteines of VKORc1 are required for complementation of ΔdsbB. HK325 (ΔdsbB) was transformed with pTrc99a carrying various cysteine mutants of rat VKORc1 (wt or A31AR deletion "Δ").

Since replacing yidC$_{A11T}$ with yidC$_{wt}$ abolishes the observed phenotype, this strain might require an additional yet unidentified mutation (or mutations) present to facilitate its promotion of VKORc1 activity. Given the known function of YidC, these results suggest that the altered YidC proteins are facilitating the proper assembly of VKORc1 in the *E. coli* cytoplasmic membrane. The gain of function of VKORc1$_{\Delta AAR}$ facilitated by the chromosomal yidC$_{T362I}$ can be reversed if yidC$_{wt}$ is overexpressed from a plasmid (FIG. 6).

Next, we asked whether the individual mutations in yidC would have synergistic effects when combined. To this end, we utilized the lambda red recombination system to construct strains that carry double yidC point mutations (T362I, T373I) and (T362I, G512S). Both of the YidC double mutant strains displayed increased VKORc1$_{\Delta AAR}$ activity compared to the single mutants, with YidC$_{T362I, G512S}$ giving higher activity than YidC$_{T362I, T373I}$ (FIG. 2, Panel C). HslV is a heat shock peptidase of the AAA+ family of peptidases. It is part of the HslVU protease complex in which HslU forms the ATPase component (19). The complex degrades defective cytoplasmic proteins under stress conditions such as heat shock. The HslV C160Y and T163I mutations obtained in our genetic selection alter two residues that are essential for the protease activity. C160 is important for the peptidase activity as well as for interaction with HslU, while T163 is involved in the essential $Zn^{2+}$ coordination; hence both mutations appear to be loss-of-function (19-20). We introduced the C160Y and T163I hslV mutations into the parental unmutagenized strain by P1 transduction as well as null alleles constructed of either hslV or hslU. These strains were tested for VKORc$1_{\Delta AAR}$ activity using the β-Gal$^{dbs}$ reporter. Indeed, HslV$_{C160Y}$ and HslV$_{T163I}$ and clean deletions of hslV or hslU behaved similarly in rendering high activity to VKORc$1_{\Delta AAR}$ (FIG. 2, Panel D). These results suggest that VKORc1, poorly assembled into the membrane, is likely recognized by the HslVU complex and degraded.

We then asked whether the hslV deletion and yid$C_{T362I}$ were synergistic in restoring the activity of VKORc$1_{\Delta AAR}$ in the HK325 background, by constructing a double mutant yid$C_{T362I}$, hslV$_{C160Y}$ (FSH231). The combination of hslV$^-$ with yid$C_{T362I}$ greatly increases the activity of VKORc$1_{\Delta AAR}$ but not VKORc$1_{wt}$ (FIG. 3, Panel A and FIG. 7). However, Western blot analysis reveals that the expression (but not activity) of VKORc$1_{wt}$ is restored to high levels in the hslV$_{C160Y}$ or yid$C_{T362I}$, hslV$_{C160Y}$ strains that are comparable to those seen with VKORc$1_{66\ AAR}$ (FIG. 3, Panel B). These results suggest that, the failure of VKORc1 to assemble into the cytoplasmic membrane of wild-type *E. coli* in a form functional in disulfide bond formation is due to a combination of inherent properties of the protein that interfere with its proper assembly and a resultant exposure of the protein to a cellular protease.

Example 4

Functionality of VKORc1 and VKORc$1_{\Delta AAR}$ in *E. coli* Strains

One reason for obtaining an *E. coli* strain expressing VKORc1 functional in disulfide bond formation was to use such a strain to readily screen for inhibitors (anticoagulants) of VKORc1 in a high-throughput blue/white agar assay in 384 well plates using the β-Gal$^{dbs}$ reporter. We recently reported this assay as a screen for inhibitors of DsbB and MtbVKOR (14). We have used this assay to test whether the strains with high functional expression of VKORc$1_{\Delta AAR}$ showed sensitivity to known anticoagulants, which would indicate that VKORc1 with the removal of amino acids 31-33 (ΔAAR) still retains a key feature of the native protein. We tested the dose-dependent inhibition of VKORc1 using two different anticoagulants, warfarin and bromindione. Both anticoagulants inhibited rat VKORc$1_{\Delta AAR}$ expressed in FSH231 with bromindione showing stronger inhibitory effects than warfarin (FIG. 4., Panel A). This result should allow convenient studies of warfarin resistance as well as high-throughput screening for novel anticoagulants that target VKORc1 using living bacterial cells.

Next we studied the mechanism of action of VKORc$1_{\Delta AAR}$ in oxidizing DsbA. In *E. coli*, under aerobic conditions menaquinone (MK) forms less than 4% of the total quinone pool in *E. coli* (22). To test whether the observed activity of VKORc1 reflects the small amount of menaquinone (MK) that is available under aerobic condition, we constructed a ΔdsbB strain deficient in MK by knocking out the gene encoding the enzyme required for MK synthesis, menA. Based on the degree of motility, VKORc1 appears to support disulfide bond formation in a ΔdsbB, ΔmenA, mutant, albeit to a slightly lesser extent than in the isogenic parental strain ΔdsbB (FIG. 8). This result implies that VKORc$1_{\Delta AAR}$ can also use ubiquinone.

We found that only the two loop cysteines and the CXXC motif, are required for VKORc$1_{\Delta AAR}$ activity in *E. coli*; loss of the other cysteines does not affect activity (FIGS. 5 and S5). As expected, the function of VKORc$1_{\Delta AAR}$ in disulfide bond formation was dependent on *E. coli* DsbA, the presumed substrate of the now functional VKORc$1_{\Delta AAR}$. To determine whether VKORc$1_{\Delta AAR}$ interacts directly with DsbA in vivo, we used a C33A mutant of DsbA which forms a detectable stable complex with DsbB and asked whether a similar scenario occurs with VKORc$1_{\Delta AAR}$ (23). We used the highly expressed VKORc$1_{\Delta AAR,\ G60D}$ lacking all nonessential cysteines expressed in a ΔdsbB, yid$C_{T362I}$, hslV$_{C160Y}$ strain (FSH231). Using a motility assay, we found that DsbA$_{C33A}$ inhibits the function of VKORc1 displaying a dominant negative phenotype in the presence of DsbA$_{wt}$ (FIG. 4, Panel B). When TCA-precipitated proteins of FSH231 strain expressing both T7-tagged VKORc$1_{\Delta AAR,\ G60D}$ and FLAG-tagged DsbA$_{C33A}$ are run on a non-reducing SDS-PAGE and probed by either anti-T7 or FLAG tags antibodies, a VKORc1-DsbA complex band around 40 kDa can be seen (FIG. 4., Panel C) that is DTT-sensitive. The complex formation is also observed when using VKORc1 lacking C51, but disappears in the absence of C46 or C132, unless the removal of C132 is accompanied by the removal of C51 (FIG. 4., Panel C). These findings indicate that loop 2 (FIG. 5) is periplasmically localized since it directly receives electrons from DsbA via a thiol-disulfide exchange reaction. Thus, all tests for the mechanism of action of VKORc$1_{\Delta AAR,\ G60D}$ functional in *E. coli* are essentially analogous to that of DsbB and bacterial VKOR and consistent with many of the studies on the functioning of VKORc1 in the endoplasmic reticulum (16, 24, 25).

Example 5

Can Other Membrane Proteins Non-Native to *E. coli* Exhibit Improved Membrane Assembly in Our Strain Backgrounds?

Our results showing poor functional expression of VKORc1 in *E. coli* are consistent with an explanation in which violation of the positive-inside rule is interfering with proper membrane protein assembly resulting in degradation. To test this explanation, we asked whether a mutation such as YidC$_{T362I}$ would facilitate membrane assembly of another membrane protein showing a similar pattern of positive-inside rule violation.

Figure 10:
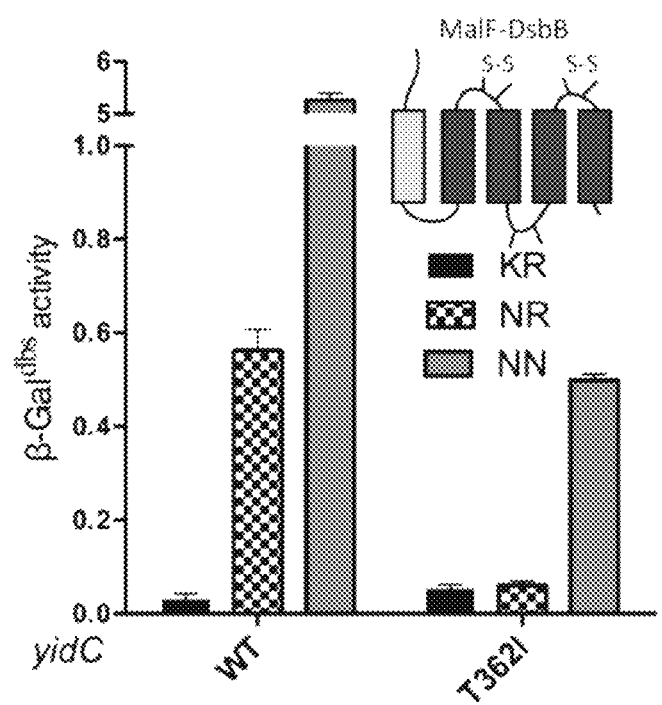
FIG. 10 contains four panels, A-D. Panel A shows YidC$_{T362I}$ restores the periplasmic activity of artificial DsbB constructs that violate the positive-inside rule. MalF-DsbB constructs K68, R72 (KR), K68N, R72 (NR) and K68N, R72N (NN) are expressed from a pTrc promoter using 1 µM IPTG. When one or more positive charges are removed from a cytoplasmic loop of MalF-DsbB fusion, DsbB exhibits lower periplasmic activity in HK325 (ΔdsbB, yidC$_{wt}$). This diminished activity can be restored by YidC$_{T362I}$ mutation (FSH229: ΔdsbB, yidC$_{T362I}$). Panel b shows YidC$_{T362I}$ relieves the toxicity of PR-Orange overexpression. Panel C shows lysate fractionation of *E. coli* strains HK325 and FSH231 expressing PR-Orange. Cells were lysed by sonication (lane 1) and spun down at 6000×g. The supernatant (lane 2) was separated from cell debris (lane 3) and subjected to ultracentrifugation (100 000×g). Soluble proteins (lane 4) were aspirated and the pelleted membranes were solubilized by 50 mM Tris buffer (pH8) containing 2% DDM (lane 5) and subjected to a second ultracentrifugation step (100 000×g). DDM-insoluble membranes were solubilized by 2% SDS (lane 6). Aliquots of fractions were then mixed with 2× Laemmli sample buffer analyzed by SDS-PAGE and visualized by coomassie staining or by fluorescence imaging using Typhoon scanner utilizing the fluorescence signal originating from the mOrange2 fusion. Panel D shows UV-Vis spectra of DDM-solubilized membrane fractions (300-600 nm).
Figure 10:
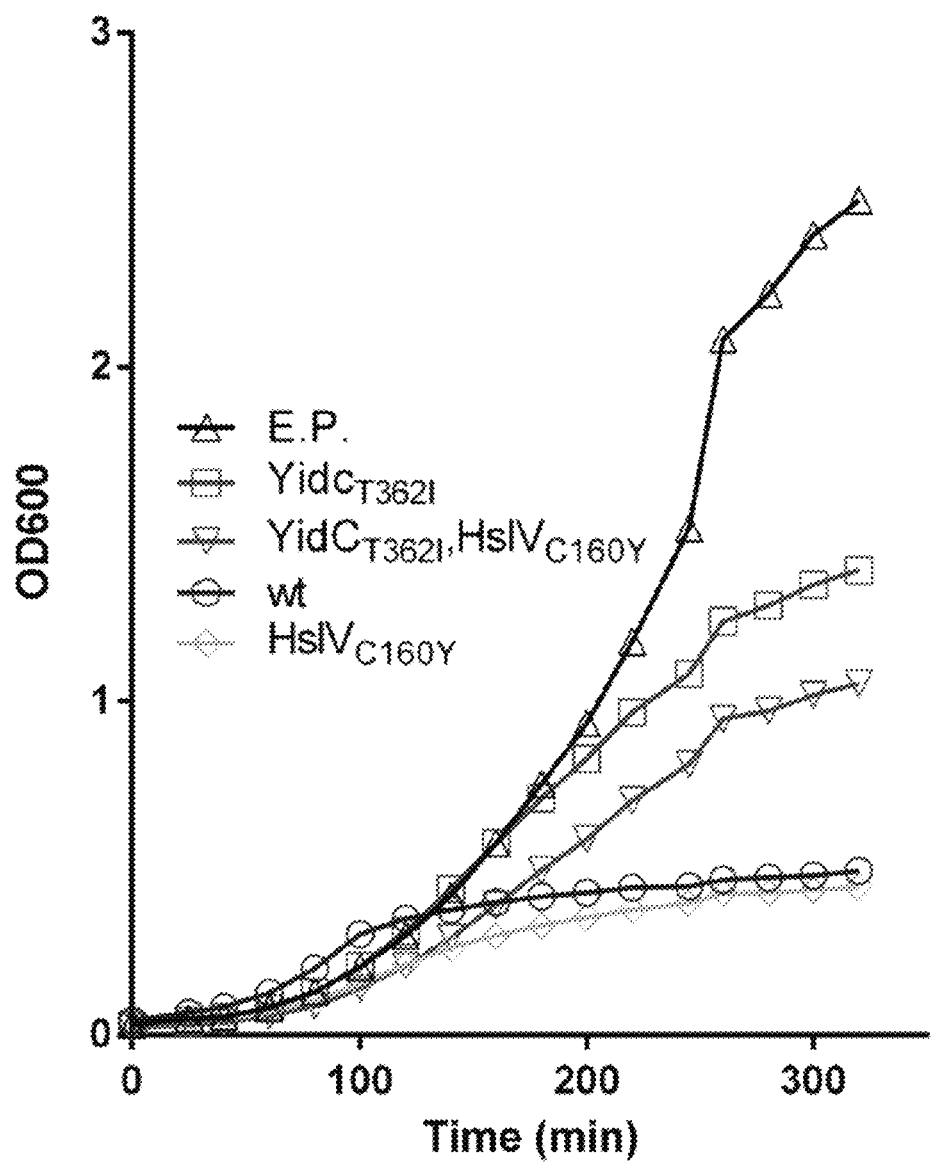
Figure 10:
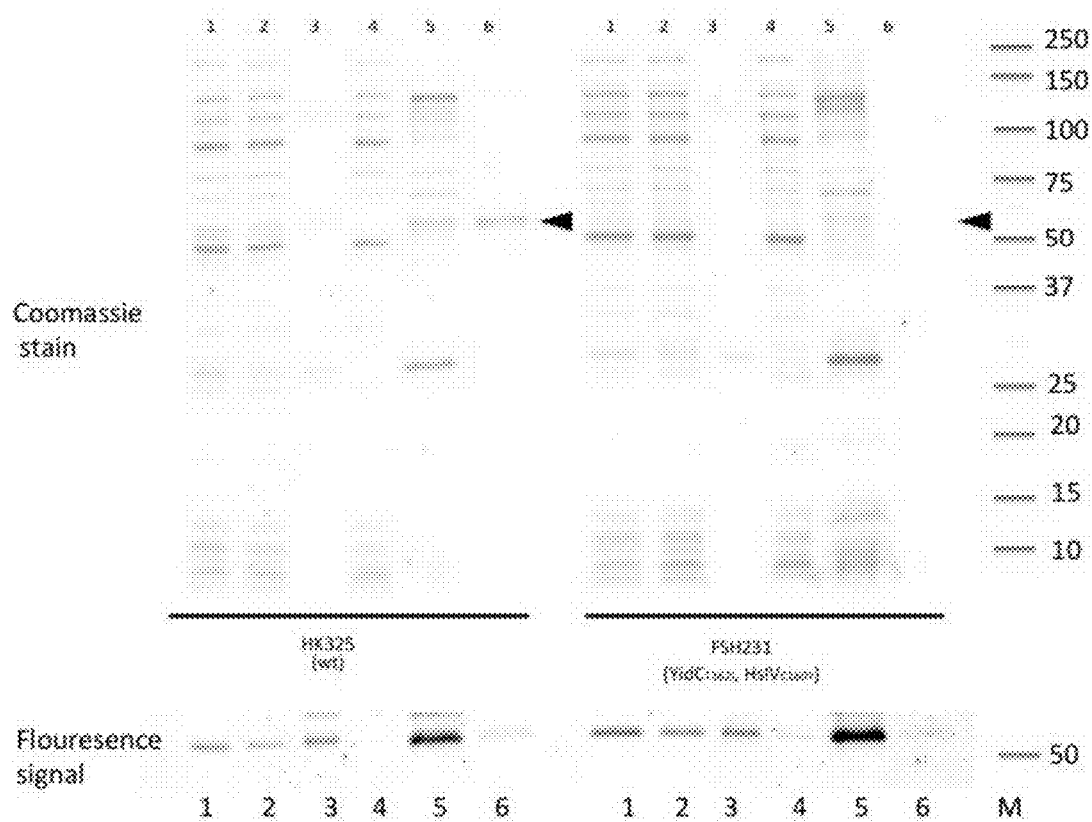
Figure 10:
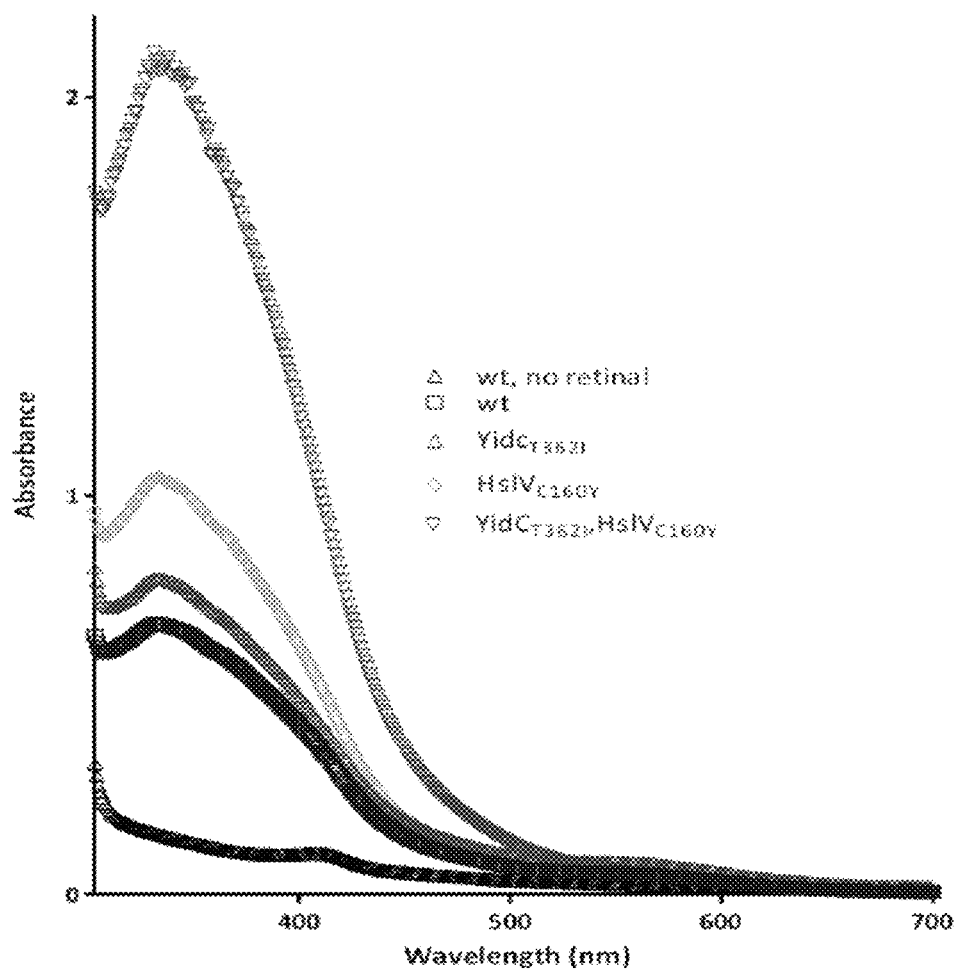

For this test, we used a previously reported construct of *E. coli* DsbB (MalF-DsbB) which is dependent on positively charged amino acids in cytoplasmic loops of DsbB for its proper orientation in the membrane, following the positive-inside rule (26). This construct, which contains the N-terminal MalF TM segment fused to the amino terminus of DsbB, is more sensitive to removal of those charged amino acids than DsbB itself (26). In particular, the activity of MalF-DsbB in the oxidation of periplasmic DsbA is quite dependent on the presence of positive charges, K68 and R72, in the short loop connecting TMH2 and TMH3. Presumably, the removal of positive charges disrupts the charge balance required to attain native membrane topology. However, when MalF-DsbB derivatives lacking K68 or both K68 and R72 (MalF-DsbB$_{NR}$ and MalF-DsbB$_{NN}$, respectively) are expressed from a plasmid in a yidC$_{T362I}$ strain, they both exhibit a significantly higher level of periplasmic activity in disulfide bond formation than expression of these constructs in a yidC$_{wt}$ strain (FIG. 10, Panel A). This finding indicates that at least the domains of MalF-DsbB$_{NN}$ which must function to oxidize DsbA in the bacterial periplasm are better localized to that compartment in the presence of YidC$_{T362I}$. The most straightforward interpretation of the results with VKORc1 and now MalF-DsbB is that the T362I change in YidC renders *E. coli* more permissive for the functional assembly of membrane proteins with soluble loops that violate the positive-inside rule.

We also examined the effect of the yidC$_{T362I}$ mutant protein and a null mutant of hsIV on the expression of proteorhodopsin (PR), a 7 TMHs bacteriorhodopsin-homolog. PR-Orange is a variant of PR that was engineered to exhibit increased fluorescent brightness when expressed in *E. coli* (See materials and methods). While the amino acids composition of this protein globally follows the positive-inside rule, some of its soluble loops do so only weakly. The overexpression of PR-Orange from a plasmid with an arabinose promoter is toxic at 0.02% arabinose concentration, causing growth cessation once *E. coli* reaches mid-log phase (FIG. 10, Panel B). However, when expressed in a yidC$_{T362I}$ strain the toxicity is markedly reduced. Expression in a hsIV$^-$ strain is even more deleterious than in an hsIV$^+$ strain, unless it is combined with yidC$_{T362I}$. Remarkably, formation of mild-detergent (DDM) insoluble PR-Orange seen upon overexpression in wild-type strain is also diminished in the double mutant strain hsIV$_{C160Y}$, yidC$_{T362I}$, (FIG. 10, Panel C). The reduction of insoluble PR-Orange is concomitant with an increase in the UV-vis absorbance of solubilized membranes, presumably as a result of accumulation of folded and retinal-incorporated protein (FIG. 10, Panel D). We cannot estimate how efficient that folding is.

Example 6

Figure 11:
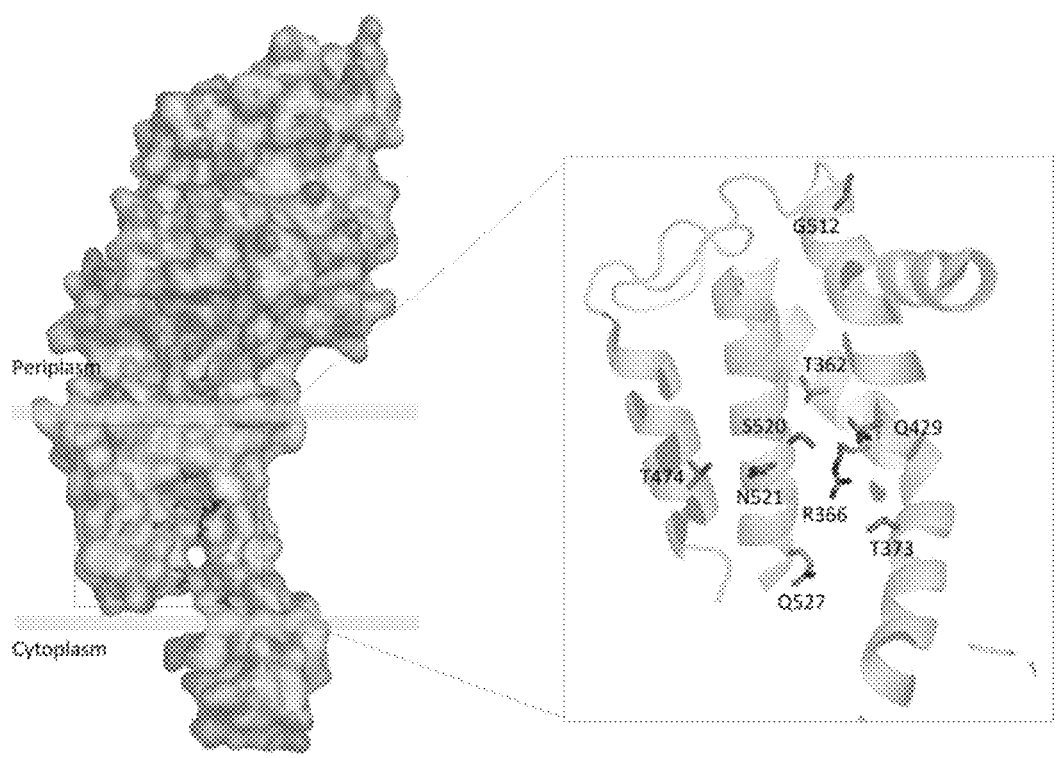
FIG. 11 shows the structure of *E. coli* YidC (PDB:3WVF). Side chains of the hydrophilic residues lining the hydrophilic groove are shown, except for G512, the main chain is shown. Cartoons are drawn using PyMOL viewer.
Figure 12:
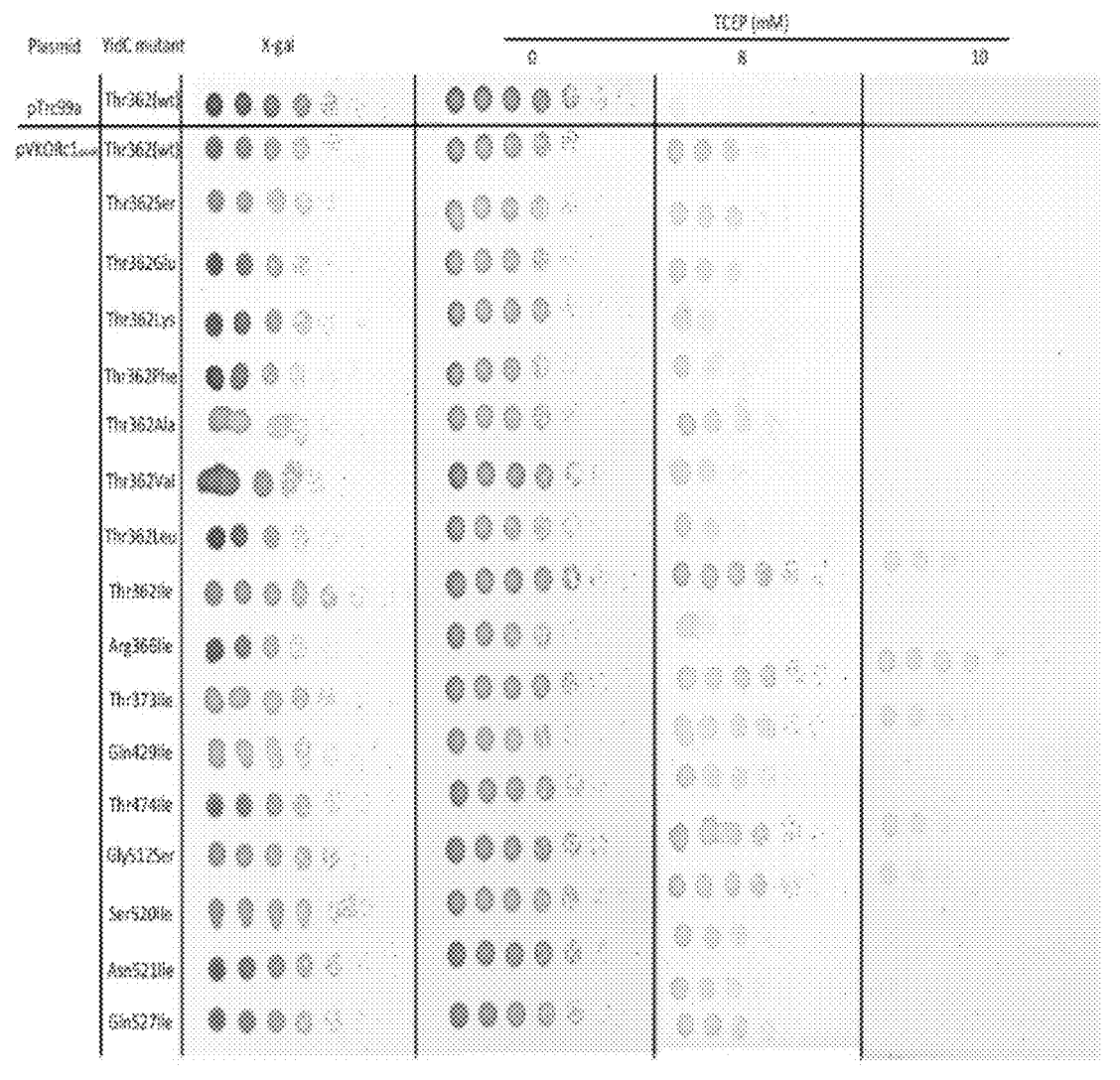

Effects of Chromosomal Directed Mutagenesis for Further Genetic Analysis of yidC Based on the recent crystal structure of YidC, two of the amino acid substitutions we obtained after the EMS treatment (T362I and T373I) are located in the membrane hydrophilic groove, which is hypothesized to accommodate portions of membrane protein substrates (FIG. 11) (27). Since two of the mutations introduce isoleucine, we tested all possible amino acids substitutions at position 362 in the chromosomal loci of yidC to see whether the introduction of an isoleucine per se is required rather than the removal of the threonines to enhance the activity of VKORc1$_{AAAR}$. In addition, we tested the activity of VKORc1 in mutant strains in which each hydrophilic residue in the membranous hydrophilic groove of YidC was mutated. All other substitutions at position 362 except S, F, A, V, L, E, and K are lethal, unless the strain is supplemented with a plasmid coding for YidC$_{wt}$. While T362I gave the highest activity among all (white color on X-Gal plate and TCEP resistance), T362A, and to a lesser extend T362S, also gave improved VKORc1$_{AAAR}$ activity to that observed with wild type YidC (FIG. 12). This suggests that it is the removal of YidC T362 that is required for VKORc1$_{AAAR}$ functional expression rather than the introduction of an isoleucine at that position. Since we obtained substitutions to isoleucine at 2 of the groove residues in our selection, T362I and T373I (besides G512S), we tried substituting isoleucine at each of the six other residues lining the hydrophilic groove R366, Q429, T474, S520, N521 and Q527 (27). All substitutions yielded functional YidC and, interestingly, two, Q429I and S520I, give increased functional expression of VKORc1$_{AAAR}$ (FIG. 12). The mutations R366I, N521I and Q527I, though they resulted in functional YidC, did not support proper assembly of VKORc1$_{AAAR}$ but rather abolished the very weak activity already seen with VKORc1$_{AAAR}$.

REFERENCES

1. Wallin E & von Heijne G (1998) Genome-wide analysis of integral membrane proteins from eubacterial, archaean, and eukaryotic organisms. *Protein Sci* 7(4): 1029-1038.
2. White S H (2009) Biophysical dissection of membrane proteins. *Nature* 459(7245): 344-346.
3. Dalbey R E, Wang P & Kuhn A (2011) Assembly of bacterial inner membrane proteins. *Annu Rev Biochem* 80: 161-187.
4. Wagner S, et al (2007) Consequences of membrane protein overexpression in *Escherichia coli*. *Molecular & Cellular Proteomics* 6(9): 1527-1550.
5. Von Heijne G (1986) The distribution of positively charged residues in bacterial inner membrane-proteins correlates with the trans-membrane topology. *EMBO J* 5(11): 3021-3027.
6. Boyd D & Beckwith J (1990) The role of charged amino-acids in the localization of secreted and membrane-proteins. *Cell* 62(6): 1031-1033.
7. Scotti P A, et al (2000) YidC, the *Escherichia coli* homologue of mitochondrial Oxa1p, is a component of the sec translocase. *EMBO J* 19(4): 542-549.
8. Serek J, et al (2004) *Escherichia coli* YidC is a membrane insertase for sec-independent proteins. *EMBO J* 23(2): 294-301.
9. Gray A N, et al (2011) Unbalanced charge distribution as a determinant for dependence of a subset of *Escherichia coli* membrane proteins on the membrane insertase YidC. *MBio* 2(6): 10.1128/mBio.00238-11. Print 2011.
10. Soman R, Yuan J, Kuhn A & Dalbey R E (2014) Polarity and charge of the periplasmic loop determine the YidC and sec translocase requirement for the M13 procoat lep protein. *J Biol Chem* 289(2): 1023-1032.
11. Hatahet H, Boyd D & Beckwith J (2014) Disulfide bond formation in prokaryotes: history, diversity and design. *Biochim Biophys Acta* 1844(8): 1402-1414
12. Dutton R J, Boyd D, Berkmen M & Beckwith J (2008) Bacterial species exhibit diversity in their mechanisms and capacity for protein disulfide bond formation. *Proc Natl Acad Sci USA* 105(33): 11933-11938.
13. Li T, et al (2004) Identification of the gene for vitamin K epoxide reductase. *Nature* 427(6974): 541-544.

14. Landeta C, et al (2015) Compounds targeting disulfide bond forming enzyme DsbB of gram-negative bacteria. *Nat Chem Biol* 11(4): 292-298.
15. Tie J K, Nicchitta C, von Heijne G & Stafford D W (2005) Membrane topology mapping of vitamin K epoxide reductase by in vitro translation/cotranslocation. *J Biol Chem* 280(16): 16410-16416.
16. Schulman S, Wang B, Li W & Rapoport T A (2010) Vitamin K epoxide reductase prefers ER membrane-anchored thioredoxin-like redox partners. *Proc Natl Acad Sci USA* 107(34): 15027-15032.
17. Tie J, Jin D & Stafford D W (2012) Human vitamin K epoxide reductase and its bacterial homologue have different membrane topologies and reaction mechanisms. *J Biol Chem* 287(41): 33945-33955.
18. Bardwell J C, McGovern K & Beckwith J (1991) Identification of a protein required for disulfide bond formation in vivo. *Cell* 67(3): 581-589.
19. Wang J, et al (2001) Crystal structures of the HslVU peptidase-ATPase complex reveal an ATP-dependent proteolysis mechanism. *Structure* 9(2): 177-184.
20. Yoo S J, et al (1998) Effects of the cys mutations on structure and function of the ATP-dependent HslVU protease in *Escherichia coli*. the Cys287 to val mutation in HslU uncouples the ATP-dependent proteolysis by HslVU from ATP hydrolysis. J Biol Chem 273(36): 22929-22935.
21. Chu P H, Huang T Y, Williams J & Stafford D W (2006) Purified vitamin K epoxide reductase alone is sufficient for conversion of vitamin K epoxide to vitamin K and vitamin K to vitamin KH2. *Proc Natl Acad Sci USA* 103(51): 19308-19313.
22. Wallace B J & Young I G (1977) Role of quinones in electron transport to oxygen and nitrate in *Escherichia coli*. studies with a ubiA-menA-double quinone mutant *Biochim Biophys Acta* 461(1): 84-100.
23. Guilhot C, Jander G, Martin N L & Beckwith J (1995) Evidence that the pathway of disulfide bond formation in *Escherichia coli* involves interactions between the cysteines of DsbB and DsbA. *Proc Natl Acad Sci USA* 92(21): 9895-9899.
24. Rishavy M A, Usubalieva A, Hallgren K W & Berkner K L (2011) Novel insight into the mechanism of the vitamin K oxidoreductase (VKOR): Electron relay through Cys43 and Cys51 reduces VKOR to allow vitamin K reduction and facilitation of vitamin K-dependent protein carboxylation. *J Biol Chem* 286(9): 7267-7278.
25. Wang X, Dutton R J, Beckwith J & Boyd D (2011) Membrane topology and mutational analysis of *Mycobacterium tuberculosis* VKOR, a protein involved in disulfide bond formation and a homologue of human vitamin K epoxide reductase. *Antioxid Redox Signal* 14(8): 1413-1420.
26. Hatahet F & Ruddock L W (2013) Topological plasticity of enzymes involved in disulfide bond formation allows catalysis in either the periplasm or the cytoplasm. *J Mol Biol* 425(18): 3268-3276
27. Kumazaki K, et al (2014) Structural basis of sec-independent membrane protein insertion by YidC. *Nature* 509(7501): 516-520.
28. Nannenga B L & Baneyx F (2012) Folding engineering strategies for efficient membrane protein production in *E. coli*. *Methods Mol Biol* 899: 187-202.
29. van Bloois E, et al (2008) Detection of cross-links between FtsH, YidC, HflK/C suggests a linked role for these proteins in quality control upon insertion of bacterial inner membrane proteins. *FEBS Lett* 582(10): 1419-1424.
30. Li W, et al (2010) Structure of a bacterial homologue of vitamin K epoxide reductase. *Nature* 463(7280): 507-512.
31. Jin D Y, Tie J K & Stafford D W (2007) The conversion of vitamin K epoxide to vitamin K quinone and vitamin K quinone to vitamin K hydroquinone uses the same active site cysteines. *Biochemistry* 46(24): 7279-7283.
32. Premkumar L, et al (2013) Rv2969c, essential for optimal growth in *Mycobacterium tuberculosis*, is a DsbA-like enzyme that interacts with VKOR-derived peptides and has atypical features of DsbA-like disulfide oxidases. *Acta Crystallogr D Biol Crystallogr* 69(Pt 10): 1981-1994.
33. Duprez W, et al (2015) Peptide inhibitors of the *Escherichia coli* DsbA oxidative machinery essential for bacterial virulence. *J Med Chem* 58(2): 577-587.
34. Kall L, Krogh A & Sonnhammer E L (2005) An HMM posterior decoder for sequence feature prediction that includes homology information. *Bioinformatics* 21 Suppl 1: i251-7.
35. Viklund H, Bernsel A, Skwark M & Elofsson A (2008) SPOCTOPUS: A combined predictor of signal peptides and membrane protein topology. *Bioinformatics* 24(24): 2928-2929.
36. Miller, J H (1992) *A Short Course in Bacterial Genetics*, (Cold Spring Harbor Laboratory Press, Plainview, N.Y.).
37. Datsenko K A & Wanner B L (2000) One-step inactivation of chromosomal genes in *Escherichia coli* K-12 using PCR products. *Proc Natl Acad Sci USA* 97(12): 6640-6645.
38. Gregg C J, et al (2014) Rational optimization of tolC as a powerful dual selectable marker for genome engineering. *Nucleic Acids Res* 42(7): 4779-4790.
39. Hochbaum, D. R., et al. (2014). "All-optical electrophysiology in mammalian neurons using engineered microbial rhodopsins." *Nature Methods* 11(8): 825-833.
40. Kralj, J. M., et al. (2011). "Electrical Spiking in *Escherichia coli* Probed with a Fluorescent Voltage-Indicating Protein." *Science* 333(6040): 345-348.
41. Shaner, N. C., et al. (2004). "Improved monomeric red, orange and yellow fluorescent proteins derived from Discosoma sp. red fluorescent protein." *Nature Biotechnology* 22(12): 1567-1572.
42. Zhao, H., et al. (1998). "Molecular evolution by staggered extension process (StEP) in vitro recombination." *Nature Biotechnology* 16(3): 258-261.
43. Omasits U, Ahrens C H, Müller S, Wollscheid B (2014) Protter: interactive protein feature visualization and integration with experimental proteomic data. *Bioinformatics*. 15; 30(6):884-886.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A host cell comprising:
   an exogenous nucleic acid molecule encoding a membrane protein, said membrane protein comprises at least one mutation; and
   wherein the host cell comprises a double mutation at T362I and T373I, or a double mutation at T362I and G512S, in the gene yidC.

2. The host cell of claim 1, wherein said host cell is a bacterial host cell.

3. The host cell of claim 1, wherein said host cell is a *Escherichia coli*.

4. The host cell of claim 1, wherein the membrane protein is selected from the group consisting of vitamin K epoxide reductase (VKORc1), proteorhodopsin, G protein couple receptors, growth factor receptors, transmembrane ion channels, neurotransmitter transporters, serotonin and olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, parathyroid hormone/parathyroid related protein (PTH/PTHrP) receptors, glucagon receptors, secretin receptors, latrotoxin receptors, metabotropic glutamate receptors, calcium receptors, gamma-aminobutyric acid B (GABA-B) receptors, pheromone receptors, histamine receptors, protease-activated receptors, rhodopsins, C—X—C Motif Chemokine Receptor 4 (CXCR4), G Protein-Coupled Receptor 3 (GPR3), vasopressin receptor, β1 adrenergic receptor, β2 adrenergic receptor, β3 adrenergic receptor, α1 adrenergic receptors and the α2 adrenergic receptor, M1 muscarinic receptor, M2 muscarinic receptor, M3 muscarinic receptor, M4 muscarinic receptor, M5 muscarinic receptor, and angiotensin II receptors.

5. The host cell of claim 4, wherein the membrane protein is VKORc1 and VKORc1 comprises a mutation having a deletion of amino acid 31-33 (AAR) (VKORc1$_{\Delta AAR}$).

6. The host cell of claim 4, wherein the membrane protein is VKORc1 and VKORc1 comprises a mutation at a residue selected from the group consisting of glycine 60 to aspartic acid (G60D), cysteine 43 to alanine (C43A), cysteine 51 to alanine (C51A), cysteine 132 to alanine (C132A), valine 29 to glutamic acid (V29E), valine 29 to lysine (V29K), arginine 33 to proline (R33P), alanine 48 to serine (A48S), arginine 53 to histidine (R53H), phenylalanine 55 to serine (F55S), serine 57 to proline (S57P), serine 57 to phenylalanine (S57F), arginine 58 to histidine (R58H), serine 52 to asparagine (S52N), arginine 61 to histidine (R61H), glycine 62 to aspartic acid (G62D), glycine 64 to aspartic acid (G64D), threonine 4 to isoleucine (T4I), leucine 65 to proline (L65P), asparagine 80 to aspartic acid (N80D), threonine 137 to proline (T137P), or combination thereof.

7. The host cell of claim 4, wherein the membrane protein is VKORc1 and VKORc1 comprises two mutations G6OD and VKORc1$_{\Delta AAR}$.

8. A cell culture comprising the host cell of claim 1.

9. A method of ligand screening, drug screening, protein capturing, protein purification, immunization, or a biophysical study, wherein the improvement comprises: utilizing the host cell of claim 1, for ligand screening, drug screening, protein capturing and purification, immunization, biophysical studies.

10. A host cell comprising:
   an exogenous nucleic acid molecule encoding a membrane protein, wherein said membrane protein comprises at least one mutation, wherein the membrane protein is vitamin K epoxide reductase (VKORc1); and
   wherein the host cell comprises a double mutation at T362I and T373I, or a double mutation at T362I and G512S, in the gene yidC.

11. The host cell of claim 10, wherein VKORc1 comprises the mutation VKORc1$_{\Delta AAR}$.

* * * * *